US010585208B1

(12) United States Patent
Yaish et al.

(10) Patent No.: US 10,585,208 B1
(45) Date of Patent: Mar. 10, 2020

(54) SYSTEMS AND METHODS FOR UNDERGROUND EXPLORATION USING COSMIC RAYS MUONS

(71) Applicants: David Yaish, Tel Aviv (IL); Amnon Harel, Haifa (IL); Yossi Kolkovich, Tel Aviv (IL)

(72) Inventors: David Yaish, Tel Aviv (IL); Amnon Harel, Haifa (IL); Yossi Kolkovich, Tel Aviv (IL)

( * ) Notice: Subject to any disclaimer, the term of this patent is extended or adjusted under 35 U.S.C. 154(b) by 89 days.

(21) Appl. No.: 15/453,908

(22) Filed: Mar. 9, 2017

Related U.S. Application Data

(60) Provisional application No. 62/306,120, filed on Mar. 10, 2016.

(51) Int. Cl.
*G01V 5/04* (2006.01)
*G01T 1/205* (2006.01)
*G01V 5/00* (2006.01)

(52) U.S. Cl.
CPC ............... *G01V 5/04* (2013.01); *G01T 1/205* (2013.01); *G01V 5/0075* (2013.01); *G01N 2223/205* (2013.01)

(58) Field of Classification Search
CPC .......... G01V 5/04; G01V 5/0075; G01T 1/205
See application file for complete search history.

(56) References Cited

U.S. PATENT DOCUMENTS

| 3,503,221 | A | * | 3/1970 | Martin | F25B 45/00 62/77 |
| 4,464,338 | A | * | 8/1984 | Dotson | G01N 33/18 250/303 |
| 4,504,438 | A | * | 3/1985 | Levy | G01V 5/04 250/256 |
| 4,670,656 | A | * | 6/1987 | Bolon | G01N 27/44717 250/374 |
| 2008/0128604 | A1 | * | 6/2008 | Bryman | G01T 1/203 250/266 |
| 2008/0191133 | A1 | * | 8/2008 | Morris | G01N 23/20 250/307 |
| 2011/0035151 | A1 | * | 2/2011 | Botto | G01V 5/04 702/2 |
| 2011/0202277 | A1 | * | 8/2011 | Haddad | G01S 13/885 702/7 |

OTHER PUBLICATIONS

Oliveira et al., First tests of thick GEMs with electrodes made of a resistive kapton, Nuclear Instruments and Methods in Physics Research A, Jun. 2007, Vo. 576, Iss. 2-3, pp. 362-366 (Year: 2007).*

* cited by examiner

*Primary Examiner* — David P Porta
*Assistant Examiner* — Jeremy S Valentiner
(74) *Attorney, Agent, or Firm* — Reches Patents

(57) ABSTRACT

A method for underground exploration using cosmic rays muons, the method comprises: detecting cosmic ray muons by sensing ionizing events that initiate within spaces of one or more gas amplification detectors of a system that is positioned within an underground space; and limiting a flow of gas within the spaces of the one or more gas amplification detectors.

17 Claims, 15 Drawing Sheets

SYSTEMS AND METHODS FOR UNDERGROUND EXPLORATION USING COSMIC RAYS MUONS

CROSS REFERENCE

This application claims priority from U.S. provisional patent Ser. No. 62/306,120 filing date Mar. 10 2016, which is incorporated by reference.

BACKGROUND

Although the underground exploration industry has made technical progress over the last decades, it is still impossible to predict with high certainty the outcome of a planned geological exploration campaign. Today due to the poor underground mapping there is still a considerable element of luck in mining exploration or high risk that a cavity or any other soft ground layers will not be mapped in civil constructions projects. The existing underground mapping techniques suffer from limited survey distance due to the high attenuation of the ground.

In mineral exploration, multiple measurements and tools are used and combined: (a) geophysical exploration: seismic reflection and refraction, gravity survey, magnetic survey using proton magnetometer, electrical resistivity and downhole logging survey; (b) geochemical exploration methods: soil sampling and stream sampling; and (c) direct exploration methods: Drilling and Mapping.

Down-hole logging surveys are made using a wide range on instruments that can be lowered into a borehole to gather information about the borehole itself and about the physical and chemical properties of rock, sediment, and fluids in and near the borehole. The down-hole logging instruments can be classified by the type measurements they perform: (a) Mechanical methods that include caliper logging and sonic logging; (b) Electrical methods that include resistivity and conductivity logging, spontaneous potential logging and measurements of induced polarization, and (c) Radioactive methods that include Natural gamma ray logging and Porosity logging using neutrons from a radioactive source The main limitation of the existing down-hole logging surveys is their limited survey distance from the borehole. There is a need to reduce the number of the drilling, and to collect as much as possible data from existing drillings in order to determine about the next steps of the drillings.

Cosmic ray muons are part of the naturally occurring cosmic radiation. Cosmic rays muons are the most-penetrating charged particles on earth. The muons arrive at the earth's surface with energies ranging from less than a GeV to thousands of GeVs. The flux of cosmic ray muons at the earth's surface is from 100 to 200 per square meter per second, depending mostly on the minimal energy considered, but also on the latitude, the weather, and other less significant variables. At the high energies relevant to underground mapping, the muons' initial directions are fairly isotropic, while at lower energies the muons tend to move towards the nadir.

Muons lose energy as they travel through matter. For muons with energies below 200 GeV, energy is lost mainly through ionization. Underground, cosmic-ray muons typically decay after reaching non-relativistic energies, for example below 0.2 GeV.

The muon energy loss is proportional to the mass of the matter the muon traversed. Due to the chemical composition of mantle rocks, the effects of the additional dependence on the chemical composition of the transversed material are negligible. The denser rocks result in larger energy loss and in fewer muons that penetrate through these rocks. Thus a map of the rates of muons arriving at an underground sensor provides a map of the weight above the sensor. This basic correspondence has been used successfully in archeology and in mapping volcanos.

The first to map rocks with muons was probably Alvarez, who searched for hidden chambers in the Egyptian pyramids. Alvarez simply divided the 2D angular phase space into discrete regions (known as "bins" in this context) and compared the observed and expected muon counts in each bin.

There is a growing need to provide reliable mapping methods.

Gaseous Detectors have shown remarkable performance in accelerator based experiments and in research labs.

These detectors require ongoing maintenance (e.g. gas flow)—and thus prior art gaseous detectors cannot and are not used on commercial and out of lab environment. Several detector technologies can be used to detect ionizing particles and measure their entry, such as scintillating fibers, ring-imaging Cherenkov detectors, and various gas detectors.

When a muon passes through a gas, it typically ionizes a few molecules per millimeter. The ionization rates roughly scale with the mass density, and so are far higher in liquids and solids.

In a gas detector, high voltage is applies across the gas so that the electrons from an ionization event are amplified in the gas, first forming an electron avalanche, then possibly a streamer, then possibly a spark. Different gas detector technologies differ in how far they allow the amplification process to go (e.g. are sparks desired or avoided), in the mechanisms used to prevent transverse growth of the shower, in the geometries of the regions with high electric fields where amplification takes place, in their preferred gas mixtures, which depend on the choices listed earlier, in the arrangement of the readout, in the removal of charges from previous signals, etc.

A detector of the Micro-Pattern Gas Detector (MPGD) family can achieve efficient and stable gas amplification, by concentrating the electrical potential difference in a small volume. In the Gaseous Electron Multiplier (GEM) family, these small volumes are holes in the GEM layer, which in the original GEN design is a film. Various gas mixtures are used in GEM detectors, typically with 70%-95% of the mixture a noble gas and one or more quencher gases such as $CH_4$, N-pentane, $CO_2$, or Dimethyl Ether.

In Thick-GEM (ThGEM) detectors, the GEM layer is a Printed Circuit Board (PCB). The GEM layers in ThGEMs can be produced using existing large-scale commercial Printed Circuit Board (PCB) production techniques. In particular, the holes are drilled, and in what followed we refer to this layer as the Drilled Board (DB).

Generic MPGDs suffer from sparks that can harm the MPGDs and the readout electronics. Sparks can also cause chemical reactions in the gas, particularly if it contains hydrocarbons, such as N-pentane, which is commonly used as a quencher gas. GEM detectors typically employ two or three amplification layers, while ThGEM can offer higher amplification per layer are typically constructed with one to three amplification layers.

The small signals ($10^4$-$10^6$ electrons) collected on the readout board must be amplified electronically. The amplifiers are best located close to the readout board, to minimize interference and capacitance on the lines that carry the small analog signals. Typically they are integrated within front-end electronics (FEE) that also digitize the signals and provide trigger information.

Some of the detectors in the ThGEM family have been designed to avoid sparks. In particular, we note the Resistive-Plate Well detectors (RPWell) and Resistive Anode Well (RWell) detectors.

In an RPWell, a plate with large volume resistivity is placed between the DB and the readouts, and signal charges are evacuated through this plate to the readouts. In an RWell, a thin coating or film with high surface resistivity is placed between the DB and the readouts, and a thin insulator (a sheet of FR4) is placed between the conductive layer and the readouts. The edges of the RWell's resistive layer are grounded, so that the signal charges are evacuated along the resistive layer to the sides. Both RPWell and RWell detectors employ a "well" geometry, where the last amplification layer is adjacent to the anode, without a gas gap between them.

Gas amplification detectors rely on gas flow in the detector to remove trace contaminations from the gas, especially electronegative gasses such as water vapor, Flour, Chlorine, and complex molecules such as hydrocarbons and halogenated hydrocarbons. Such contaminations can arise from internal leaks, from environmental materials permeating through the seals, and from outgassing from the detector components. The latter includes any electronics and wiring within the gas volume. Gas contaminations can degrade detector performance through two main mechanisms. First, such contaminants can capture electrons in the gas. In the drift gap they can capture ionization electrons before they reach the DB, and in the DB they can reduce the effective gain, in either case, reducing the detector's efficiency at any operating voltage. The second mechanism is through the electron avalanches, which can induce chemical reactions in some contaminants. For example, hydrocarbons might polymerize, releasing soot which can settle on the DB and result in sharp conductive edges on its electrode. Such edges might reduce the maximal voltage maintained in the DB below the minimal operating voltage. The sensitivity of the detector to the different chemicals varies by over an order of magnitude, so concepts such as the "total contaminant concentration" are of little use, and when such numbers are quoted here, they should be taken as indications of possible values.

There is a need to provide improved detectors.

SUMMARY

Systems, detectors and method as illustrated in the specification and/or the claims.

There may be provided a method for underground exploration using cosmic rays muons, the method may include detecting cosmic ray muons by sensing ionizing events that initiate within spaces of one or more gas amplification detectors of a system that may be positioned within an underground space; and limiting a flow of gas within the spaces of the one or more gas amplification detectors.

The method may include preventing the flow of the gas by positioning the one or more gas amplification detectors within a sealed housing.

The method may include limiting the flow of the gas by positioning the one or more gas amplification detectors within a sealed housing.

The method may include limiting a rate of the flow of the gas to below 5 liter a day.

The method may include cleaning, by forcing a flow of the gas through the one or more spaces of the one or more gas amplification detectors, during multiple cleaning periods, wherein each cleaning period may be followed by a non-flow period during which the flow of cleaning gas may be stopped.

The duration of a non-flow period may exceed a duration of the cleaning period.

The gas amplification detector of the one or more gas amplification detectors may include outgassing materials that limit a total outgassing rates of the gas amplification detector below $5 \cdot 10^{-5}$ cc atmosphere per second The gas amplification detector of the one or more gas amplification detectors may include at least one seal that exhibits a lower permeability than a Nitrile Rubber seal.

The gas amplification detector of the one or more gas amplification detectors may include one or more internal component that may be made of Polyether ether ketone.

The method may include passing the gas through a first manifold positioned at one end of a gas amplification detector of the one or more gas amplification detectors, over multiple front-end electronics and through a drift gap and to a second manifold that may be positioned at an opposite edge of the gas amplification detector.

The manifold of the first and second manifold may include an opening that may include a height that changes as a function of a distance from a center of the manifold.

The system may include a longitudinal axis; wherein the one or more gas amplification detectors may include a group of gas amplification detectors; and wherein each gas amplification detector of the group may include a length, a width and a depth, wherein the length and the width exceed the depth by at least a factor of ten.

The group may include gas amplification detectors that may be substantially parallel to the longitudinal axis and gas amplification detectors that may be substantially normal to the longitudinal axis.

The gas amplification detectors that may be substantially parallel to the longitudinal axis may include gas amplification detectors that may be substantially parallel to each other.

The gas amplification detectors that may be substantially parallel to the longitudinal axis may include gas amplification detectors that may be substantially normal to each other.

The gas amplification detectors that may be substantially parallel to the longitudinal axis may include gas amplification detectors that surround the longitudinal axis from four sides.

The one or more gas amplification detectors may include at least one thick gaseous electron multiplier (ThGEM) detector.

The limiting of the flow of the gas within the spaces of the one or more gas amplification detectors may include preventing the flow of the gas within the spaces of the one or more gas amplification detectors.

The method may include generating information about the ionizing events.

The method may include transmitting the information about the ionizing events.

The method may include processing the information about the ionizing event to provide a three-dimensional estimate regarding a content of an underground medium that may be located above the system.

The processing may be responsive to at least one out of geophysical information and information that was gained by another system about the content of the underground medium.

The other system may include one or more sensors that differ from gas amplification detectors.

The processing may include data fusion of the information about the ionizing events and Ground-Penetrating Radar data related to a content of at least an upper portion of the underground medium.

The data fusion may be responsive to a reference three-dimensional model of the underground medium.

The processing may be responsive to at least one property of a cavity containing the system.

The data fusion may be responsive to uncertainties of a reference model and to dependence of said uncertainties on location.

The mapping uses an explicit regularization term that quantifies a disagreement between the map and the a-priori model.

The method may include generating inverted data related to the underground model.

The method may include performing data fusion between the information about the ionizing events information from another source.

The information from the other source may be geophysical information about the content of the underground medium.

The data fusion may include using information about uncertainties related to the geo-physical information.

The method may include resolving kernels with weighting functions that reflect the uncertainties related to the geo-physical information.

The information from the other source may be information that was gained by another system about the content of the underground medium.

The data fusion may include using information about uncertainties related to the information that was gained by the other system.

The method may include resolving kernels with weighting functions that reflect the uncertainties related to the information that was gained by the other system.

The method may include supplying the gas from an underground pressurized gas vessel.

The pressurized gas vessel may be attached to the detector.

The method may include evaluating the gas using a pump.

The pump maintains a gas pressure of 0.2-0.9 atmospheres in the detector.

There may be provided a system that may include one or more detectors for detecting cosmic ray muons by sensing ionizing events that initiate within spaces of one or more gas amplification detectors of a system that may be positioned within an underground space; and one or more gas flow limiters for limiting a flow of gas within the spaces of the one or more gas amplification detectors.

There may be provided a method for underground exploration using cosmic rays muons, the method may include: detecting cosmic ray muons by sensing ionizing events that initiate within spaces of one or more detectors of a system that may be positioned within an underground space; generating information about the ionizing events; processing the information about the ionizing event to provide a three-dimensional estimate regarding a content of an underground medium that may be located above the system; wherein the processing of the information may be responsive to additional information about the underground medium; wherein the additional information may be obtained from an information source that differs from the ionizing events and may be tailored to underground medium. The system may or may not include gas amplification detectors.

There may be provided a computer program product that stores instructions that once executed by a computer cause the computer to execute the steps of detecting cosmic ray muons by sensing ionizing events that initiate within spaces of one or more detectors of a system that may be positioned within an underground space; generating information about the ionizing events; processing the information about the ionizing event to provide a three-dimensional estimate regarding a content of an underground medium that may be located above the system; wherein the processing of the information may be responsive to additional information about the underground medium; wherein the additional information may be obtained from an information source that differs from the ionizing events and may be tailored to underground medium.

Any reference to detection of cosmic rays muons may be applicable to the detection of gravitational waves.

For example—there may be provided a method for underground exploration using gravitational waves, the method may include detecting gravitation waves by one or more gravitational sensors; generating information about the gravitational waves; processing the information about the gravitational waves to provide a three-dimensional estimate regarding a content of an underground medium; wherein the processing of the information may be responsive to additional information about the underground medium; wherein the additional information may be obtained from an information source that differs from the sensing of the gravitational waves and may be tailored to underground medium. The system may be located below the underground volume, above the underground volume, underground or above the surface.

There may be provided a computer program product that stores instructions that once executed by a computer cause the computer to execute the steps of detecting gravitation waves by one or more gravitational sensors of a system; generating information about the gravitational waves; processing the information about the gravitational waves to provide a three-dimensional estimate regarding a content of an underground medium; wherein the processing of the information may be responsive to additional information about the underground medium; wherein the additional information may be obtained from an information source that differs from the sensing of the gravitational waves and may be tailored to underground medium.

There may be provided method for underground exploration using cosmic rays muons, the method may include: detecting cosmic ray muons by sensing ionizing events in systems placed in one or more wells with diameters up to 20 cm; generating information about the ionizing events; processing the information about the ionizing event to provide a three-dimensional estimate regarding a content of an underground medium that is located above the lowest detection system.

The wells may be PQ boreholes.

BRIEF DESCRIPTION OF THE DRAWINGS

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE DRAWINGS

Figure 1:
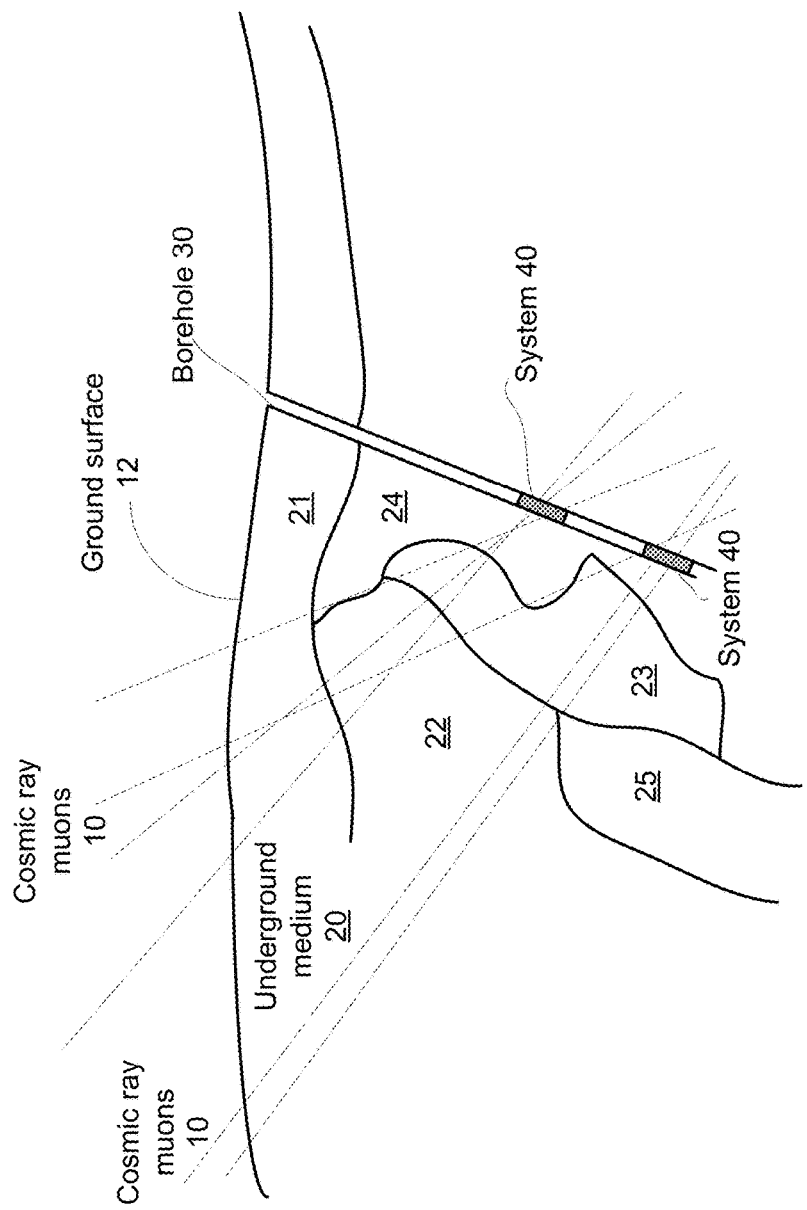
FIG. 1 is a cross sectional view of two systems that are positioned in a borehole and receive cosmic ray muons that pass through an underground medium according to an embodiment of the invention.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The term "comprising" is synonymous with (means the same thing as) "including," "containing" or "having" and is inclusive or open-ended and does not exclude additional, unrecited elements or method steps.

The term "consisting" is a closed (only includes exactly what is stated) and excludes any additional, unrecited elements or method steps.

The term "consisting essentially of" limits the scope to specified materials or steps and those that do not materially affect the basic and novel characteristics.

In the claims and specification any reference to the term "comprising" (or "including" or "containing") should be applied mutatis mutandis to the term "consisting" and should be applied mutatis mutandis to the phrase "consisting essentially of".

For example, any system illustrated in any of the figures can be limited to the components illustrated in the figures, can also have unspecified elements that do not materially affect the basic and novel characteristics or may have additional, unrecited elements.

In the claims and specification any reference to the term "consisting" should be applied mutatis mutandis to the term "comprising" and should be applied mutatis mutandis to the phrase "consisting essentially of".

In the claims and specification any reference to the phrase "consisting essentially of" should be applied mutatis mutandis to the term "comprising" and should be applied mutatis mutandis to the term "consisting".

Any reference in the specification to a method should be applied mutatis mutandis to a system capable of executing the method.

Any reference in the specification to a system should be applied mutatis mutandis to a method that may be executed by the system.

The term "substantially" or "about" can refer to an accuracy (or deviation) of any value between 1 and 20 percent.

The term "proximate" may refer to a range of distances that may span, for example, between a fraction of a millimeter and less than 5 centimeters.

Any combination of any components of any of the systems illustrated in any of the figures may be provided.

There is provided a new type of underground sensors based on cosmic ray muons detection with new algorithms to fuse the muon data with other geophysics sensors data to extend significantly the detection range of the currently used instrumentation for underground mapping. There is a need for the technology in the geology/underground research and for commercial use such as in mineral exploration, civil engineering, $CO_2$ ground storage, and other geology research. Several designs of this new type of detector are described, for various underground usages.

The detectors may be used in various scenarios. For example—in civil engineering projects, it can be useful to map the properties of the underlying rock.

In particular, it is desirable to ensure that no cavities lie beneath the foundations of buildings, such as bridges or sky scrapers. Another example arises in tunnel digging, where unexpected cavities can damage the tunnel digging machinery. Similarly, when re-excavating an existing mine, the newly dug tunnel can encounter existing, unmapped mine shafts.

There is provided a method that may perform mapping of underground soil and rock densities using muons. These maps can then be used to extract information on the depths of geological layers, on cavities, on ore deposits etc.

FIG. 1 is a cross sectional view of two systems 40 that are positioned in an inclined borehole 30 and receive cosmic ray muons 10 that pass through an underground medium 20 according to an embodiment of the invention. Using multiple systems 40 may allow to reconstruct a three-dimensional mapping of the underground medium 20. Underground medium 20 is delimited by ground surface 12 and may include different parts (for example 21, 22, 23, 24 and 25) that can include different materials and/or have different density. The system 40 may be any of the systems illustrated in the specification.

Figure 2:
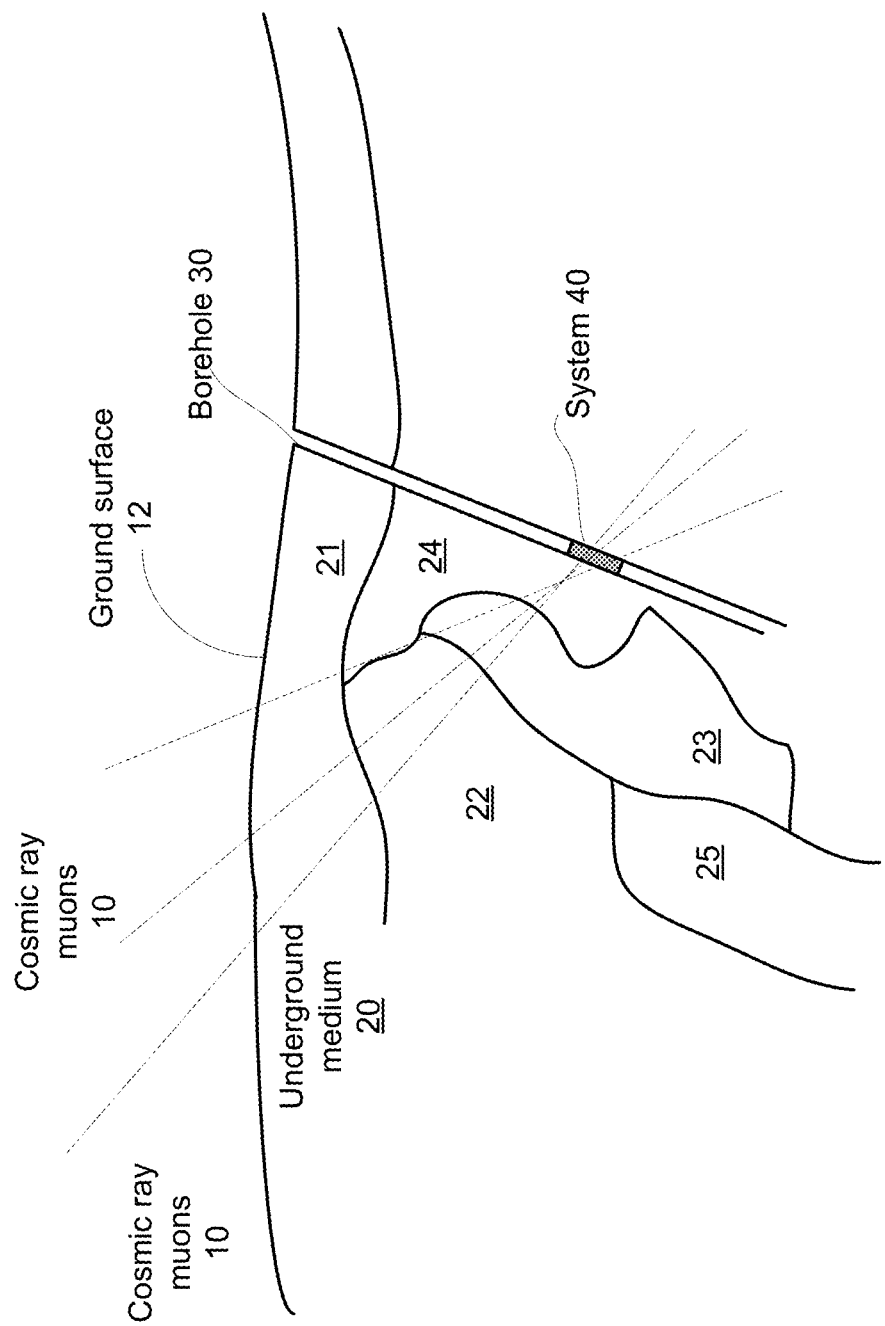
FIG. 2 is a cross sectional view of a system that is positioned in a borehole and receive cosmic ray muons that pass through an underground medium according to an embodiment of the invention.

FIG. 2 differs from FIG. 1 by showing only a single system 40.

Figure 3:
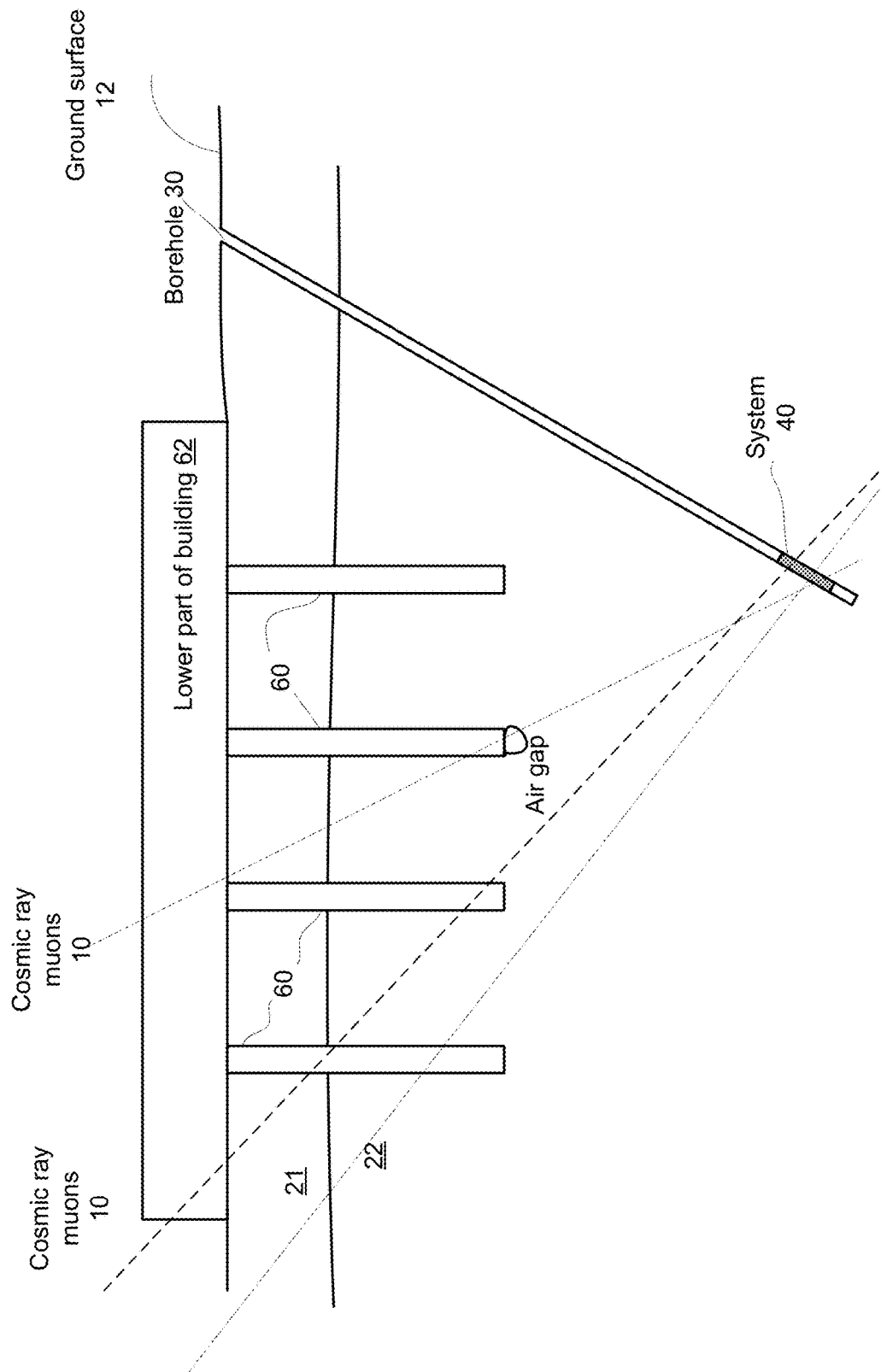
FIG. 3 is a cross sectional view of a system that is positioned in a vertical borehole and receive cosmic ray muons that pass through an underground medium and through the ground beneath a building site according to an embodiment of the invention.

FIG. 3 is a cross sectional view of a system 40 that is positioned in an inclined borehole 30 and receive cosmic ray muons that pass through an underground medium and through parts of a building according to an embodiment of the invention. FIG. 3 illustrates that cosmic muon rays 10 pass through the lower part of the building 62 and through foundations 60 and even through an air gap. The underground volume includes two layers 21 and 22.

Figure 4:
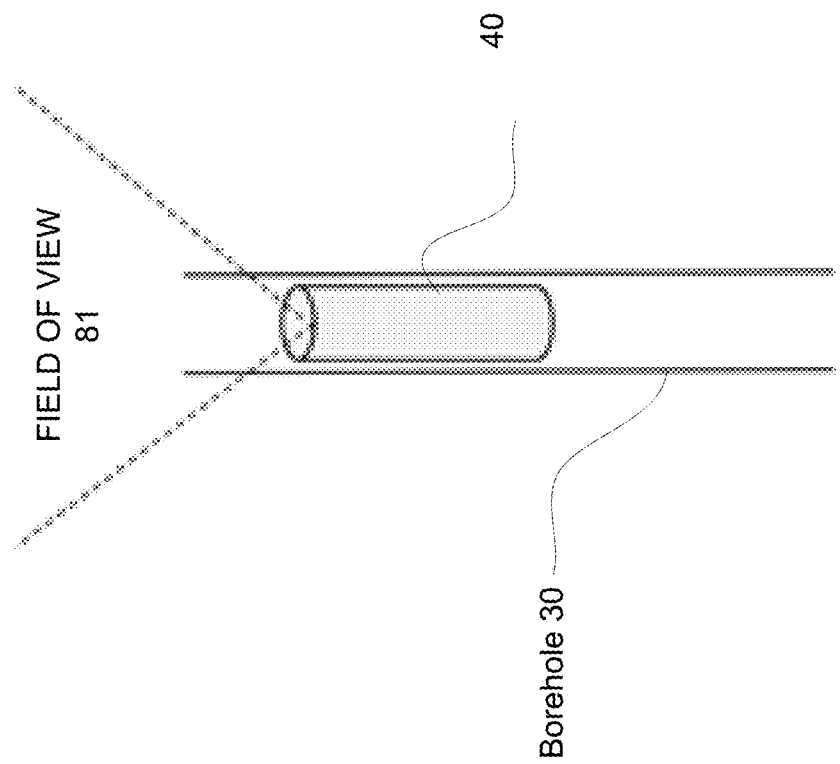
FIG. 4 illustrates two cross sections taken within planes that are normal to each other and illustrates a field of view of a system that is positioned in an inclined borehole and receive cosmic ray muons according to an embodiment of the invention.
Figure 4:
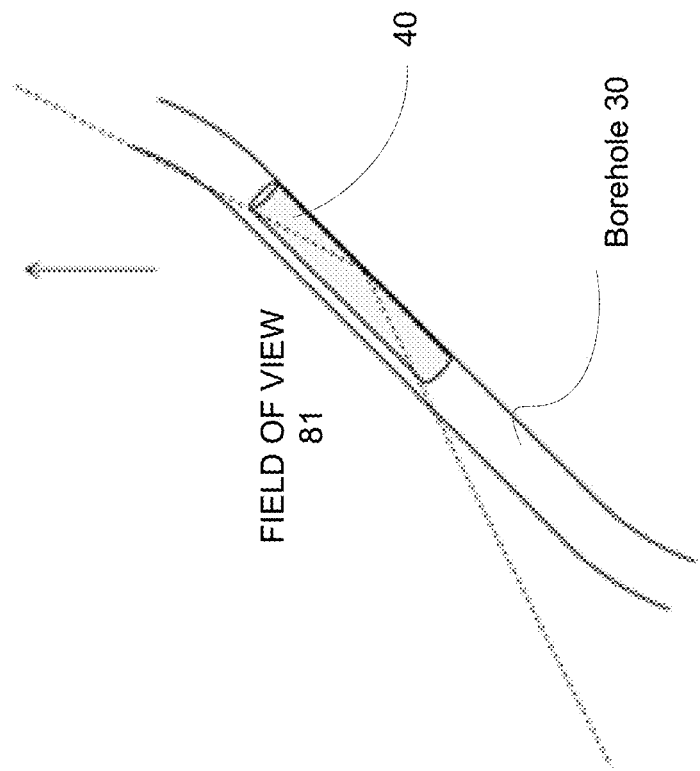

FIG. 4 illustrates two cross sections taken within planes that are normal to each other and illustrates a field of view of a system that is positioned in an inclined borehole and receives cosmic ray muons according to an embodiment of the invention. This system may include detectors that are parallel to each other—such as system 41 of FIG. 5. This system (also referred to as two-sided arrangement) may have significant blind spots in the plane of the detectors. This weakness is of less importance when slanted boreholes are available. The detectors should be placed as horizontally as possible, resulting in the good coverage shown in FIG. 4 (left image).

Sealed and reduced gas-flow gas-amplification detectors

Standard gas-amplification detectors require constant gas supply and evacuation to maintain the gas purity. This presents logistical problems when the detectors are in inaccessible underground locations. One of the common contaminant is water vapor, which is an electronegative gas. Hence humidity in the gas mixture can capture electrons in the drift gap before they are amplified, and should be kept low.

A sealing system which is adequate in air, where the absolute humidity is of order of 10 mbar, might prove inadequate under several atmosphere of water. Such submersion might occur due to groundwater, which may further rise while the detector is deployed. Furthermore, the evacuation of gas from the detector is problematic. The gas evacuation must be accomplished without allowing air to diffuse back into the detectors. At the surface, and in mining shafts, this is easily accomplished by keeping the detector at pressure slightly above the environmental pressure (say, 1.02 atm at sea level) and using bubblers. But this solution will fail when the outside pressure is higher. Alternatives include using a pump to evacuate the gas, and running a gas outlet line to the surface. To avoid contamination from the long gas line to the surface, the gas outlet line must have low permeability and outgassing.

To reduce the gas contamination various measures were taken. One of these measures include using of $CO_2$ as a quencher. Specifically, CO2 is a satisfactory quencher in Argon-based mixtures. The detector may use Ar—CO2 gas mixtures, with 70 to 95% argon. This avoids the more expensive Neon gas mixtures while offering a fairly high ionization rates.

The standard substrate of PCB boards, which form parts of the detector, is a compound material typically made of glass fibers and epoxy. Due to their complex structure and the presence of the epoxy, foreign materials such as water molecules can easily adhere to the substrate and be trapped in various configurations within it. This leads to high outgassing rates and hence PCB boards are considered unsuitable for high vacuum systems. Not only are such boards a key component of the ThGEM concept, they are also useful for the FEE in other gas detectors, such as the various Micro-Pattern Gas Detectors (MPGDs).

Thus, it may seem that significant outgassing is unavoidable in ThGEMs, and that significant gas flow is a necessary to maintain gas purity. However, it has been found that it is possible to drastically reduce outgassing in a gas detector using and adapting technology from the high-vacuum field. This makes it possible to operate some ThGEM detector in sealed mode, with no gas flow. Even when gas flow is unavoidable, the amount of gas required is reduced, resulting in a more flexible system that is cheaper to operate.

For example, an underground detector may be placed underground together with a pressurized vessel filled with premixed gas that can suffice for its operation over weeks, months, or years. The same applies to MPGDs and other gas detectors that include electronic components in the gas volume and/or that are operated underground.

To achieve low gas contamination requires appropriate design, and commissioning. Low gas contamination allows operation in one of three modes:

Sealed mode is the easiest to operate, and greatly simplifies the overall detector system as neither gas supply nor gas evacuation is required. However, sealed mode operation requires very low gas contamination rates. Thus both an extensive commissioning and a meticulous design which avoids internal contamination from trapped gas volumes (e.g. under screw tips) are required. Relatively large gas volumes are advantageous in sealed mode, as a given mass of contamination results in lower relative impurity.

Low flow mode is similar to that used in most existing MPGDs, except that the low contamination rate achieved via the design and commissioning allows a lower flow rate. As the detector efficiency, and hence detection rates, degrade gradually in the presence of electronegative contaminants, the gas flow can be controlled dynamically as needed to restore full detector efficiency. Some additional or minimal flow may be required to avoid degradation through other mechanisms, such as polymerization. For example, the flow may suffice to replace a volume of gas equal to the gas vessel's volume every 1 to 10 days. For comparison, an ordinary initial flushing of a gas detector, or any gas system with similar gas purity requirements, flushes a volume of gas equal to 8-10 the gas vessel's volume. So this example is equivalent to refilling the detector every 8-100 days. For comparison, a recent study at CERN indicated that the ideal gas flow rate for the GEM under study is between 100 and 5000 times higher. We attribute this difference to the design and commissioning of our detectors, as described in this patent. For example, a detector along the lines of FIG. 9 has an internal gas volume of about 5 liters, and requires a flow of 0.5 to 5 liter per day.

Intermittent flow mode is similar, except that the detector is operated with zero flow (as in sealed mode) for significant periods of time. Between periods of zero flow, the detector is flushed so that its gas volume is replaced up to ten times. As in low flow mode above, the timing and/or rate and/or duration of the gas flow can be controlled dynamically as needed by monitoring the detection rates. The average flow is in the same range as for the low flow mode above, but this mode can simplify the design of the control system and when dynamic control is used it extends the range of responses.

The gas flow in non-sealed detectors may be optimized to efficiently clean the drift gap with a minimal amount of gas. For example, using entrance and exit manifolds that direct the incoming gas to the drift gap and that guide the gas to flow past the entire detector plane by increase the flow resistance along the shorted paths, as demonstrated in FIG. 5. The location-dependent flow resistance can be provided by a slot with a varying width, or by varying the diameter and spacing of holes leading to/from the drift gap.

Figure 5:
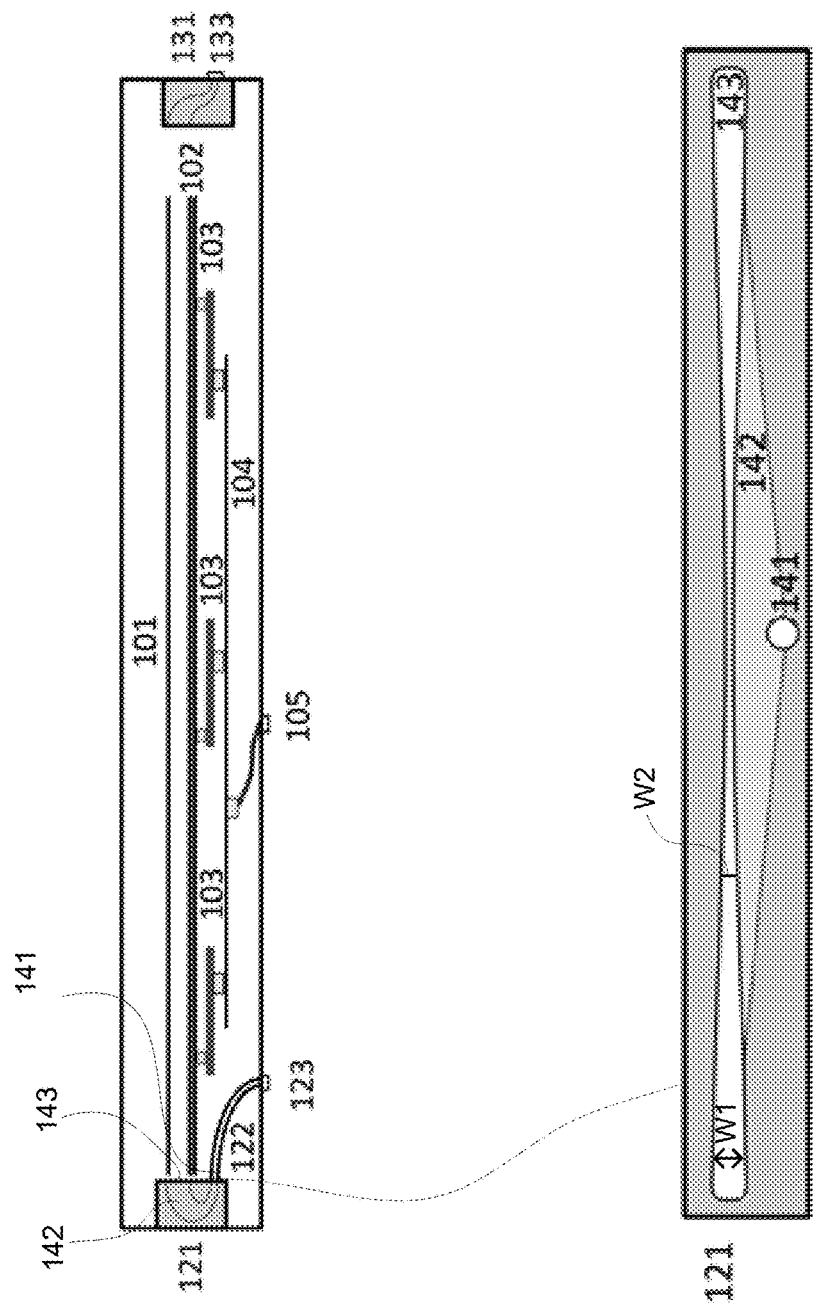
FIG. 5 is a cross section of a system and a view of a manifold of the system according to an embodiment of the invention.

The two-manifold solution is demonstrated for a flat detector, as useful for mineshafts, in FIG. 5. FIG. 5 schematically shows the internals of a detector configuration suitable for this outer shape, including a cathode 101, drilled board (DB) and an adjacent readout board that are collectively denoted 102, FEE boards 103, an interconnect board 104, and an outgoing data connector 105, with the electrical signal connectors between them shown in gray boxes and a data ribbon indicated by the black-gray striped band.

FIG. 5 further shows a gas inlet 123, an inflow manifold 121, a gas line between them 122, an outflow manifold 131, and gas outlet 133. In this illustration the gas inlet is located on the large face of the detector while the outlet is on a narrow face, but in practice they are likely to both be on the narrow faces or both on the large face.

FIG. 5 (low part) also illustrates a possible implementation of the manifold 121, with the gas entrance 141 that connects to the gas line 122, the inner gas path 142 and the exit slot 143 which is located directly opposite the drift gap (between the cathode 101 and the DB) and may be in contact with the cathode 101, DB, and an adjacent readout boards. Due to the high voltages on the cathode and DB, the part of the manifold that is close to them must be a good insulator. The material should also have low outgassing. For example, the manifold can be constructed from PEEK, which is also easily machinable. Using similar manifolds and optionally, also gas lines, a gas flow that efficiently flushes the drift gaps can also be achieved in other detector shapes, such as in borehole detectors.

Design for Low Gas Contamination

To achieve low gas contamination rates, the detectors are designed to minimize internal, outgassing, and external leaks. Internal leaks are due to trapped gas volumes. Gas is often trapped inside insulated cables and below the tips of screws. We avoid trapping gas by using drilled or slotted screws, high-vacuum grade insulated high-voltage cables, etc.

To minimize outgassing, high-vacuum grade materials are used whenever possible. In particular, the gas vessel is made from either a high-vacuum-grade stainless steel alloy such as 304, 304L, or 316L, or a high-vacuum-grade aluminum alloy such as 6061-T6. Aluminum's high thermal conductivity and lower hydrogen permeation make it the default choice, but stainless steel allows a wider choice of seal technologies. The vessel surface may be electropolished and/or degreased as in high-vacuum systems. Due to the high-voltage used in gas amplification, most of the mechanical structure (supports, fasteners, manifolds, gas lines, etc.) must be made of insulators, such as plastic. However, Nylon and many other plastic materials are to be avoided. Whenever possible, low-outgassing plastics such as PEEK and Teflon are used in the mechanical structure. In some cases, metal parts made from suitable alloys are also be used. Commercially available high-vacuum grade insulated and shielded cables were noted above as a tool for avoiding internal leaks and are also useful for their low outgassing.

To minimize external leaks, we avoid the standard Nitrile-Rubber O-rings, and use high-vacuum seals such as fluoroelastomer O-rings or metal seals. Similarly, we use vacuum-grade data and power connectors and gas valves.

Commissioning for Low Gas Contamination

In vacuum and high-vacuum systems, accelerated outgassing is performed at temperatures above 250 Celsius. Such outgassing cannot be used for the gas detectors as the PCBs and electronics comprising the detector cannot withstand temperatures above 130-180 Celsius, depending on manufacturing details and the rate of heating. Reducing the outgassing rates allows us to reduce the gas flow rates and in some cases to avoid it altogether and work in sealed mode.

It has been found that milder accelerated outgassing suffices for the operation of GEM detectors. For example, the detector may be pumped to vacuum using a turbo pump and backing pump combination while it is heated for 120-150 Celsius for over several days, a week or more, than allowed to cool gradually for over a day or more while pumping out any gas. During this procedure, pressures below $10^{-3}$ Torr were reached. More generally, accelerated outgassing using vacuum in the 0.1 to $10^{-6}$ Torr range is combined with temperatures of up to 180 Celsius is performed, which reduces the outgassing from the detector materials (including the housing and the electronics) once the detector is in operation. The duration of the outgassing may be predetermined. Alternatively, the outgassing can progress until reaching various stopping criteria, such as achieving a desired pressure, or observing that the pressure rise rate when the pumping is stopped and requiring that the rate is lower than some threshold, such as $10^{-3}$ Torr in 10 minutes. This threshold can be calculated from the level of contaminations that degrades the detector performance and its planned usage time (e.g. months, years). However, due to the varying effects of the various possible contaminants, it is usually better to set it from practical experience.

More standard procedures can also help. Some of the PCBs can be pre-baked at 180 Celsius, which ensures that the epoxy in their substrate is fully cured, thus reducing the outgassing associated with the slow curing process that occurs in room temperatures. To shorten the accelerated outgassing procedure, all of the PCBs can be pre-dried temperatures up to the tolerance of their components, which is 150 Celsius in our current designs, and the detector can be assembled in a dry room.

The Detectors

To achieve stable long-term operation boreholes and other underground locations, precise measurements of muon entry directions, and reduced production costs, there may be provided a family of gas detectors of the "RPWELL" and "RWELL" variations that incorporate the design considerations described above to achieve low gas contamination rates.

A non-limiting example of a detector is illustrated in US patent application titled "Large Scale Gas Electron Multiplier and Detection Method", Ser. No. 14/966,084 which is incorporated herein by reference.

To simplify construction, only a single amplification layer (DB) is used in a well configurations. The gas gap between the DB and the cathode is known as the drift gap, as electrons ionized by the muon in this gap are guided towards the holes in the DB by the configuration of the electric field. To avoid sparks, the detectors can be constructed as RPWell or RWell detectors.

The Detection System

The complete detector system (or a single gas vessel, in the case of a borehole) is designed to measure the muon's location in at least two planes. Each detection plane provides a 2D location of its ionization event on its plane, and the 3D trajectory of the muon can be reconstructed as a straight line connecting the locations measured on different detection planes. Each detector plane comprises one or more spaces of one or more gas amplification detectors.

The size and shape of the detector is determined by its underground location. Mineshaft offer relatively large spaces with ~1 atm of air. This allows the use of large rectangular detectors, large spacing between the detectors, relatively easy access to the detectors, and offer space for nearby support machinery such as gas and high-voltage supplies. The large spacing permits fine angular resolution with limited spatial resolution in each detector. For example, 0.5 m separation and a spatial resolution of 3 mm result in angular resolutions better than 10 mrad.

Figure 6:
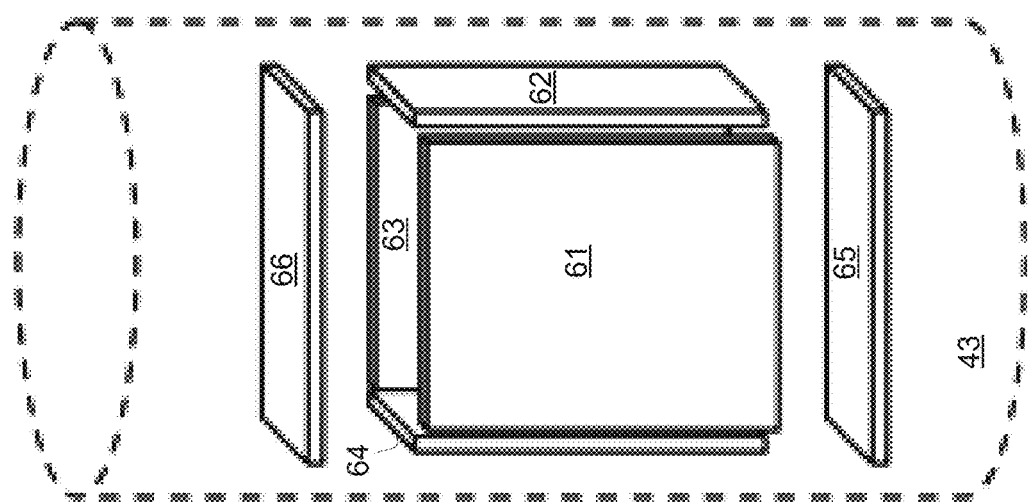
FIG. 6 illustrates various arrangement of different detectors of different systems according to various embodiments of the invention.
Figure 6:
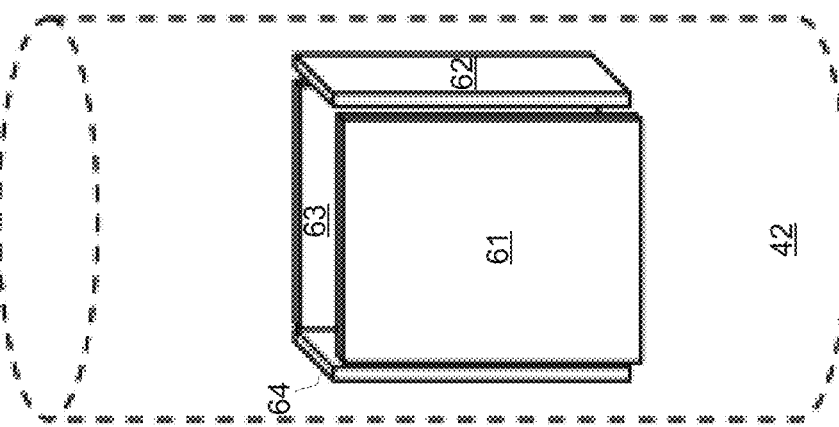
Figure 6:
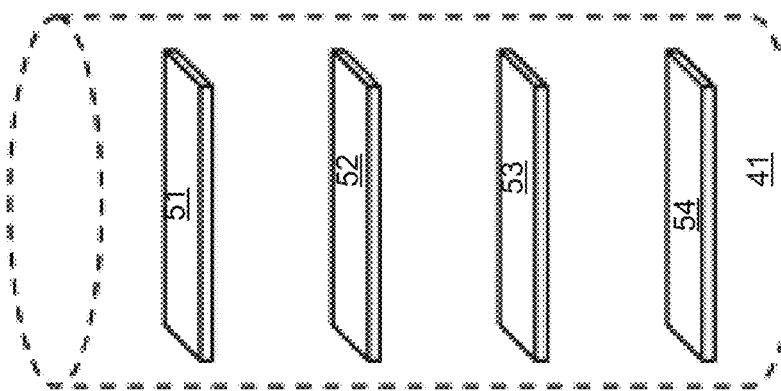

Some mining operations can dig wide wells with diameters of 30-70 cm or more, which allow various detector configurations based on rectangular detectors with edge sizes such as 25 or 65 cm or more. Some of the possible configurations are shown in FIG. 6:

a. System 41 includes four horizontal detector planes 51, 52, 53 and 54. This configuration may provide excellent coverage for directions within ~45° of the zenith. This system has a simple and repetitive structure. Can produce 1 and/or 2 layer units and deploy as many as needed.

b. System 42 includes four vertical detector planes 61-64 that are include two pairs of detector planes. Detector planes 63 and 61 are parallel to each other and normal to detector planes 62 and 64. This configuration provides good coverage for all directions at least 10-20° away from the zenith c. System 43 includes six detector planes—two horizontal detector planes 65 and 66 and four vertical detector planes 61-64. The four vertical detector planes may be positioned between the two horizontal detector planes 65 and 66. This configuration provides good coverage for all directions. A similar configuration with one of the horizontal plane detectors 65 or 66 removed, provides good coverage for directions that are 5-10° away from the zenith. However, the complicated geometry requires more intricate design.

The number of detector planes, the relative angle between the detector planes, the orientation of the detector planes may differ from those illustrated in FIG. 4. For example— the angle between two detector planes may range between zero and 180 degrees. The detector planes may have the same shape and size or may differ from each other by at least shape and/or size.

All the angles and/or orientations of FIG. 6 refer to a system that is vertical. When the system is positioned at a different orientation—the orientation of the detector planes may change.

All offer sizable separation between detector planes, so that spatial resolutions of 2-5 mm can easily suffice for underground mapping needs Boreholes are the most common and the most challenging environment for underground detectors. The detectors must be rugged enough to survive transportation and insertion into the borehole, as well as the possibility of being flooded by groundwater at pressures of several atmospheres. The widest of the standard widths is the "PQ" with a nominal diameter of 122.6 mm. This limits the area of the detectors and hence the data collection rate. Furthermore, some leeway must remain to maneuver the detector, and the detector body must be rugged and several mm thick. In soft ground, the borehole may be reinforced to avoid its collapse, further reducing the internal diameter available for the detectors.

Figure 7:
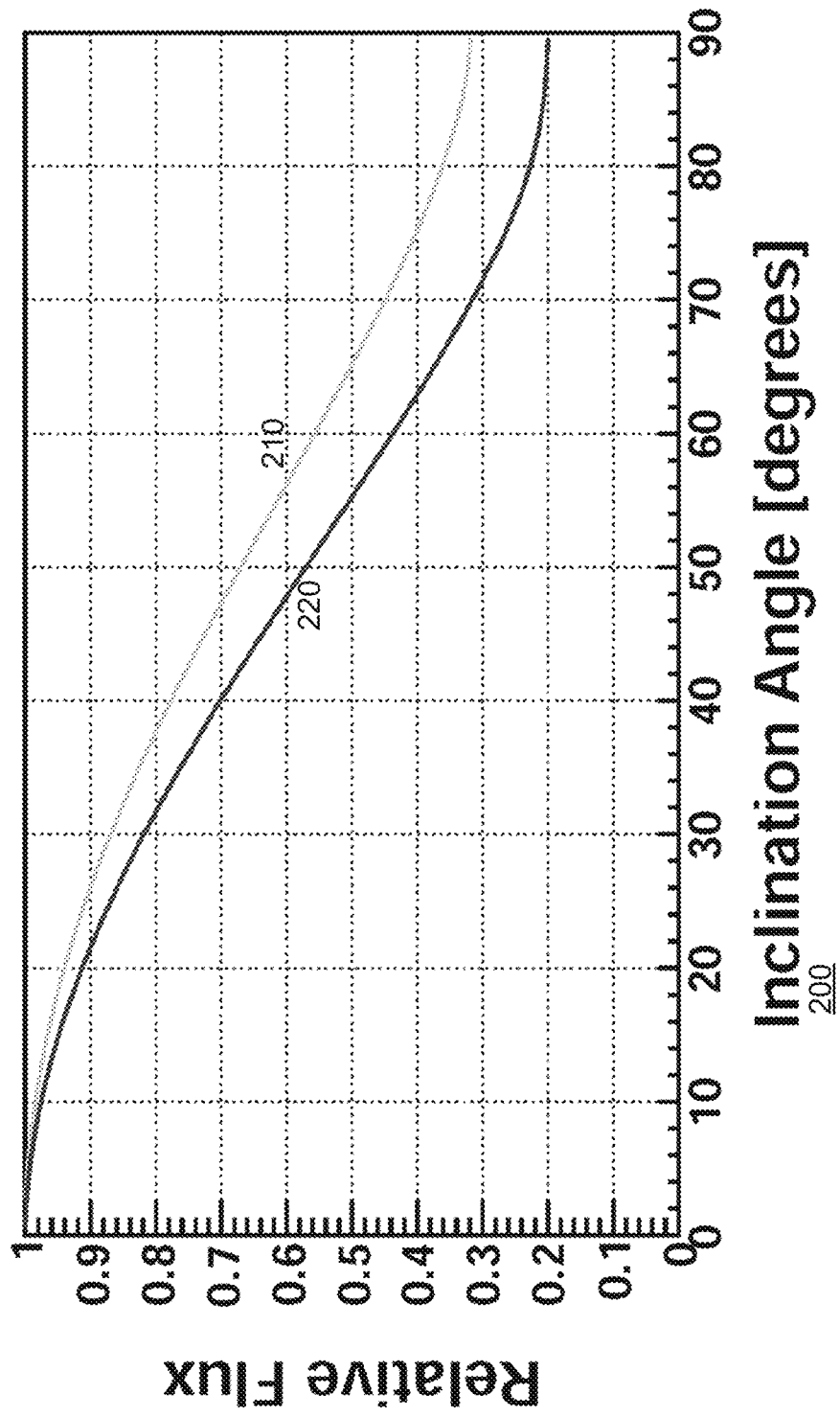
FIG. 7 illustrates the relationship between a relative flux of cosmic ray muons received by a detector and the orientation (inclination angle) of the detector in relation to the horizon.

In this narrow geometry, the detector boards are best placed vertical, despite the fact that the rate of muons through two vertical boards is 3-5 times lower than through the same two boards when they are oriented horizontally. The muon collection rate can be increased by placing the detectors in a slanted borehole. Even a moderate slope significantly increases the muon yield, as demonstrated in graph 200 of FIG. 7. Curve 210 is for a single detector plane and curve 220 is for two detectors planes in a possible borehole geometry.

Figure 8:
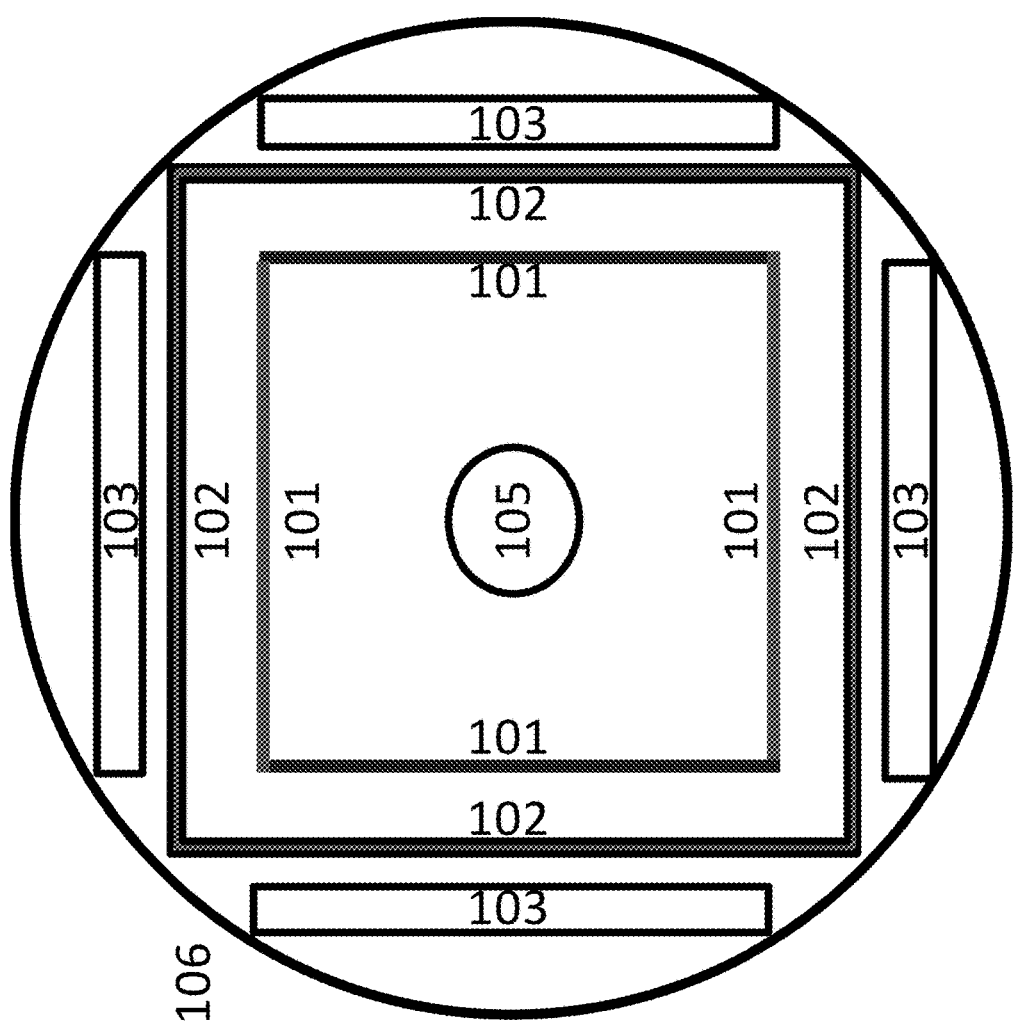
FIG. 8 is a top view of multiple detectors of a system according to an embodiment of the invention.

Taking for example the four-sided configuration whose cross section is shown in FIG. 8, and taking into account the full detector structure including its front-end electronic, opposite sides are less than 10 cm apart, and a spatial resolution below 2 mm can be useful in some application. Starting from the middle of FIG. 8, we have space reserved for wires leading to additional components beneath those shown in the cross section, the cathodes 101, the drift gaps, the DBs and readout boards, with each DB and adjacent readout board collectively denoted 102 and shown as a single unit, and the FEE boards 103, all within a cylindrical gas-tight vessel 106. This arrangement maximizes the volume available for the front-end electronics (FEE). The FEE boards in this design can be constructed as part of a single flex board, along the lines detailed in the next paragraph.

The boreholes do not always run straight, and do not always maintain their nominal widths over time. The typical detector length, including the on-board electronics, HVPS, and the mechanical components outside the gas volume, is over 1 meter. Inserting such a long cylinder into an uneven borehole requires significant clearance, and for such boreholes, even narrower detectors are useful.

Figure 9:
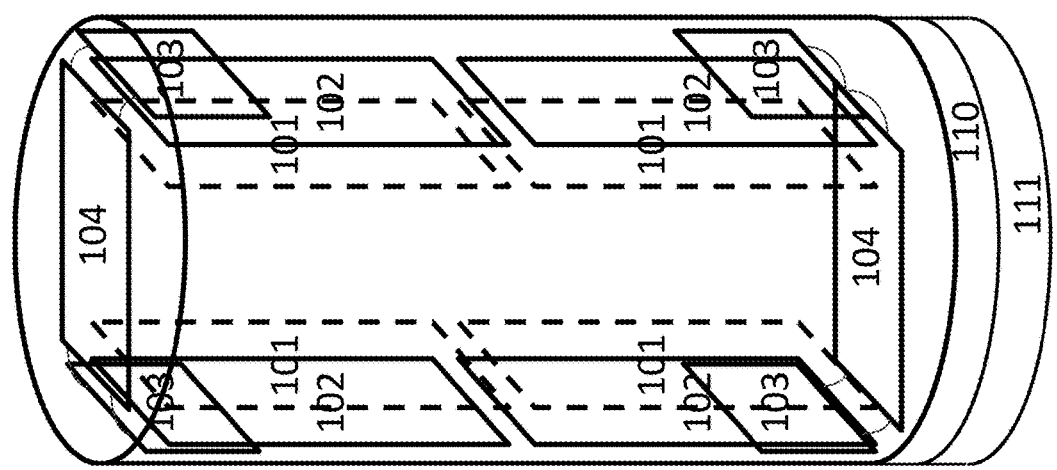
FIG. 9 illustrates an arrangement of different detectors of a system according to an embodiment of the invention.

A tighter two-sided arrangement suitable for such narrow detectors is shown in FIG. 9. In addition to the cathodes 10, DB and adjacent-readout board collectively denoted 102, and FEE boards 103 and vessel 106 shown before, here we also show an interconnect board 104 that connects to the FEE boards via flexible connectors, allowing each FEE-interconnect-FEE combination to be produced as a single flex-board using standard PCB manufacturing techniques. We also show the locations of the High-Voltage Power Supply unit (HVPS—110), and the on-board computer (OBC—120) which controls the FEE and collates their output.

Figure 10:
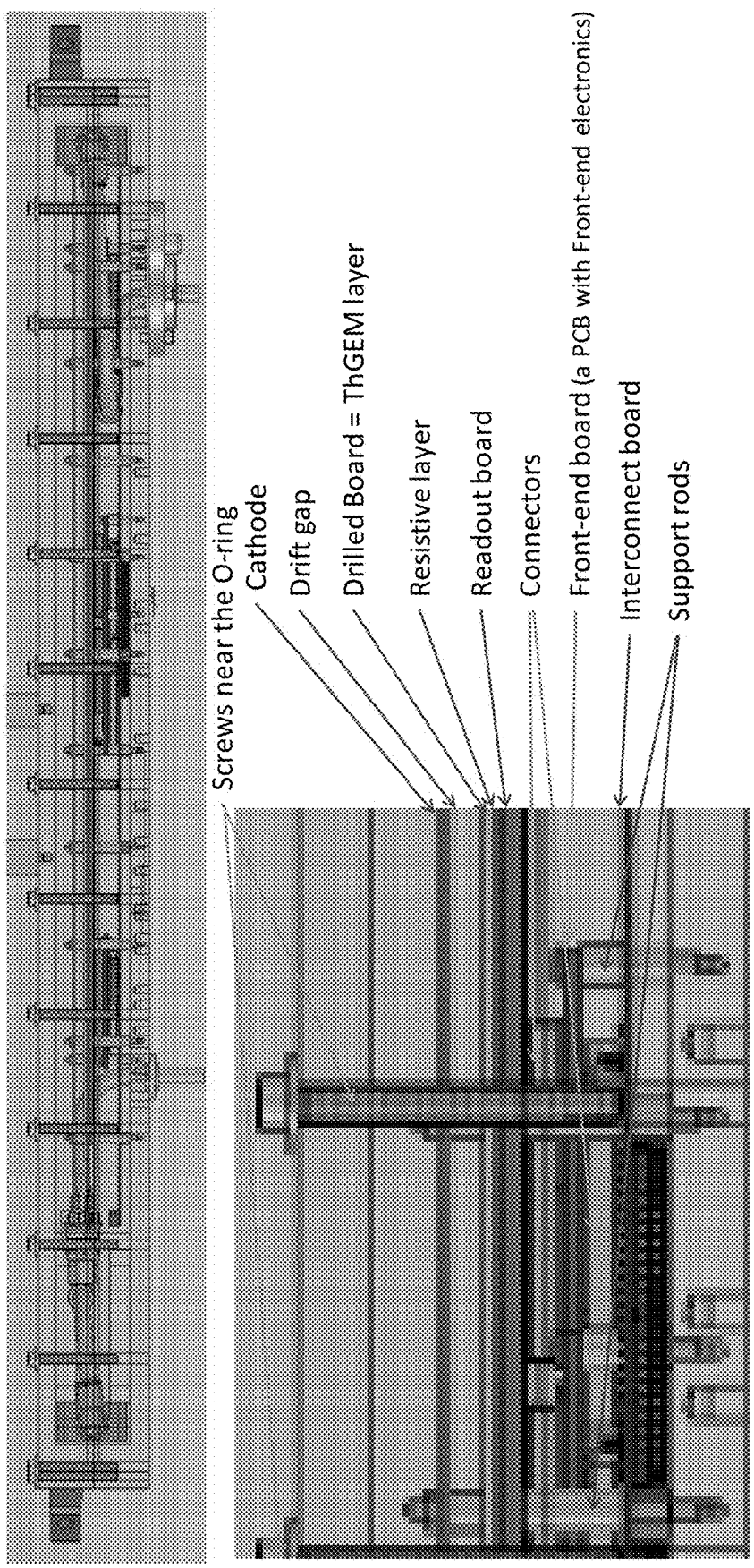
FIG. 10 is a cross sectional view of a system according to an embodiment of the invention.

FIG. 10 illustrates a system according to an embodiment of the invention.

An exhaust pump can be used to evacuate the gas from the detector. The pump may be a. Attached to the detector itself, minimizing the length of the gas line between them, thus reducing its flow resistance and gas contamination due to permeation through the gas line.

b. On the ground surface, as detailed below.

c. In an intermediate depth. This may be useful to ensure that the gas outlet is above any groundwater and/or to protect this equipment from theft when it is left unattended for long periods of time.

Placing the gas evacuation on the surface offers several advantages: (a) simplifies the underground system, (b) the system can operate in a watery environment, (c) simplified maintenance for the gas evacuation system and (d) the detector can be operated in pressures below 1 atm, such as 0.2-0.8 atm. In such low pressures, the detector can operate in lower voltages, for example ~500V instead of ~2000V.

Placing the gas supply on the surface offers several advantages: (a) simplifies the underground system, (b) simplifies the maintenance of the gas supply system, such as exchanging gas bottles, (c) provides ample room for a gas mixing system so that simpler and more standard gases can be purchased and mixed on site.

FIG. 10 illustrates a development box that includes extra functionality (that may not be included in the system), such as the ability to survive vacuum in the lab.

At the top of FIG. 10 there is a cross-section two support bars that are screwed into the lid—those are there to reduce deformation under vacuum (in room conditions). It also includes an extra-large vacuum opening, seen on the bottom right. And it supports all modes of operation, so in addition to the large opening for the vacuum pump, it has gas entrances (one is clearly seen on the bottom left, one half-hidden on the bottom right), gas lines, and manifolds.

The top board is the cathode. Below it is the drift gap, then the drilled board (DB), then the readout board, then the connectors from the readout board to the front-end boards (FEBs), then five FEBs. Only three are clearly visible, but there are three of them in the middle. Below them are the connectors from the FEBs to the interconnect board, then the interconnect board.

The "sandwich" part, from the cathode to the readout board, is described in US patent application publication number US20160170078 A1 (FIGS. 1-4).

On the sides of the drawing there are handles. The prominent vertical screws are holding the two parts of the box together. The O-ring between the two halves was hidden to see more of the structure. The vertical parts are spacers around support rods which hold the various boards in place and press the DB together with the readout board. There's a combined data & HV port on the bottom right, near where there's a gas exit and the large vacuum opening.

Figure 11:
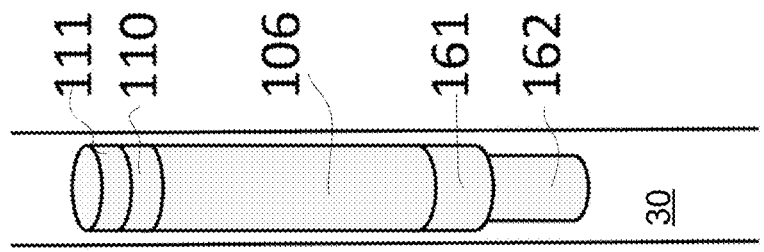
FIG. 11 illustrates various parts of two systems according to embodiments of the invention.
Figure 11:
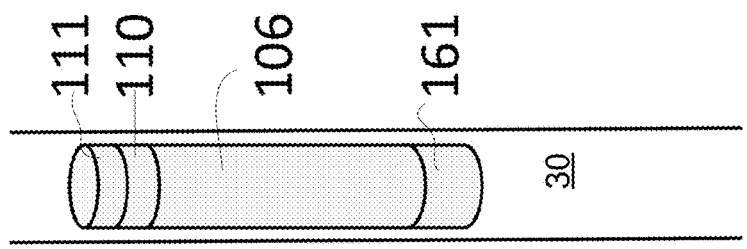

FIG. 11 illustrates two configurations—in the left configuration a pump housing 161 is attached to the detector, which includes a gas vessel 106, a High-Voltage Power Supply (HVPS) unit 110 and an electronics box with an on-board computer (OBC) 111. The right configuration further illustrates a pressurized container of premixed gas 162.

Figure 12:
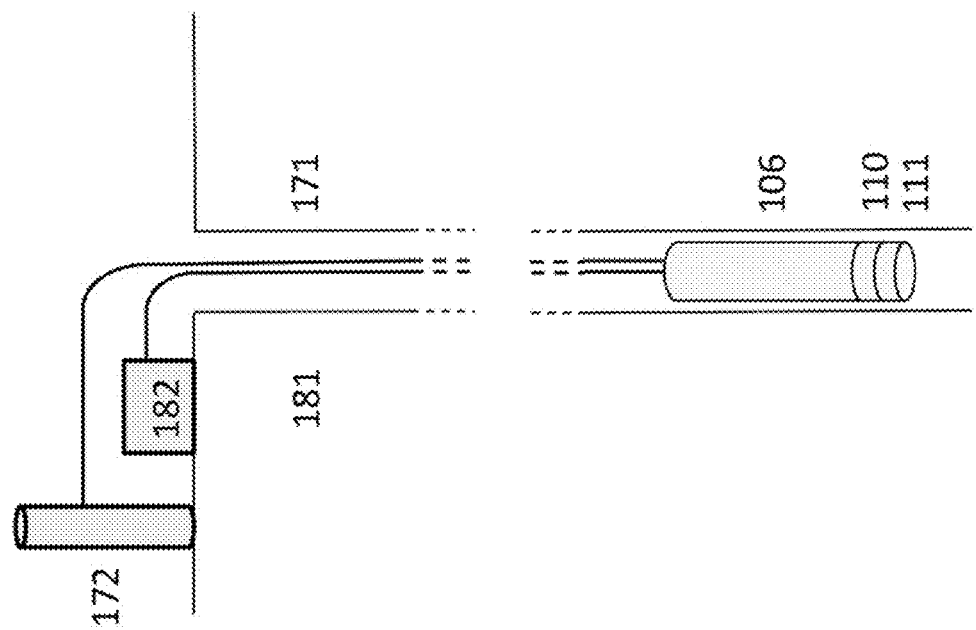
FIG. 12 illustrates a system with above ground gas supply and evacuation according to an embodiment of the invention.

FIG. 12 illustrates such a system with both the gas supply and evacuation above ground. The illustrated system uses a premixed, pressurized gas, in the container 172. From the pressurized gas container, the gas goes through a regulator and a valve (not pictures) to the inflow gas line 171 and from there to the gas vessel 106. An HVPS unit 110 and an OBC unit 120 are shown below the gas vessel 106. Gas exits the gas vessel 106 through an outflow gas line 181 which ends at the evacuation pump 182.

The Mapping

There may be provided a method and system for mapping the underground medium. The mapping method may be executed by the system illustrated above, by a system that receives the information from the system illustrated above and/or by a system that include cosmic ray muon detectors that differ from the system illustrated above.

The data collected by the muon detectors can be used to map the rock (and soil) densities around them. The simplest mapping technique, in the spirit of Alvarez' work, is to plot the 2D distribution of the directions of the incoming muons arriving to each detector. Specifically, the plot can show the observed muon count per bin relative to the expected counts. Adapting this approach to our method for underground mapping, the expectation is calculated using the known ground surface contours and any other additional information included in an input reference model. The raw difference and their statistical significance (Z test statistic) can both be useful.

The ground surface contours can have a dramatic effect due to the large density difference between ground and air. It is equally important (and implied above) to accurately map the cavity in which the detector is placed. This is trivial and easy if the detector is located in an easily accessible cavity, such as a mine shaft. But can be more difficult in boreholes and other drilled holes that are not perfectly straight, whether their turns are by accident or by design. In some green field explorations, winding boreholes are the rule, rather than the exception. In these cases the cavities hosting the muon detectors should be mapped using other instrumentation (cameras, gravitometers, etc.).

3D maps are produced from the results from several detectors, using any additional information included in an input reference model, and any available gravitometry model. Since gravitometry also measures mass densities, its data can naturally be combined with muon data in any 3D mapping technique (see for example [Jourde, Gibert, Marteau 2014 and references therein]).

3D mapping typically requires longer exposure times for each detector. The details of the uncertainties on the inputs shape the appropriate inversion algorithm. Inversion algorithms differ in their choice of (often implicit) regularization, which suppresses the large small-scale fluctuations typical in unregularized inverted data, functioning as a low-pass filter. In particular, while the space of possible maps has infinite dimensionality, the space of maps considered by any reasonable mapping algorithm is of a dimension smaller than the finite size of the data. The space of maps considered can simply be $(\mathbb{R}^+)^N$ where is N is the number of voxels considered, or it can be any linear combination of a suitable chosen set of maps, as in the resolving kernel approach. In all cases, the very choice of the space of maps under consideration is a key implicit regularization. For example, the size of a side of a voxel sets the minimal length scale for the reconstructed map.

The choice of regularization technique(s) (e.g. Bayesian vs. explicit, absolute counts vs. ratio above expectations), shape (e.g. reduction of content squared, or of the second derivative), and strength depend on the specific use case. For example, in some geological scenarios it may be helpful to have the regularization "penalize" rapid horizontal changes in the mass density more severely than vertical changes.

Ground-Penetrating Radar (GPR) can provide high quality maps of the top layers, with the penetrating depth depending on the exact soil and rock composition, its water content, etc. The geophysicist can them summarize this information, and any other available pertinent data, as a 3D model of the upper layers. This model can be incorporated in the 3D muon, or muon and gravitometry map by either (a) adjusting the resolving kernels so they ignore this region and adjust the measurements to account for the expected effects of this region, or by (b) defining explicit regularization terms that "penalize" solutions according to their disagreement with this model.

The uncertainties on a geo-physical model are far from uniform. For example:
a. The top layers, and the regions near bore holes may be well-mapped using the various surveying sensors deployed there.
b. The density of the soil layers (say, at depths of 0.5-1.5 m) may be well known from direct sampling.
c. The rock composition in boreholes may be well known from direct sampling
d. The density of the upper layers may be indicated by GPR data
e. The unevenness of the terrain can result in significant uncertainties on the densities at ground level.
f. The density of soil and porous rocks may be affected by changing groundwater levels.

The extrapolation from the well-measured locations to other locations may have various distinct uncertainties. While the properties (thickness, density) of horizontal sedimentary layers may be easily interpolated, the properties of intrusive rocks are less certain as their shapes are more varied and their composition varies on smaller length scales.

Thus, when combining muon data with the a-priori data summarized in the geo-physical model, it is important to include detailed model uncertainties in the quantification of the disagreement between the a-priori model and the reconstructed map. In particular, these uncertainties should vary as a function of the underground location 3-vector $\vec{r}$.

As an explicit example, let us assume an a-priori 3D model $m(\vec{r})$ (derived for example, from GPR) with the Gaussian uncertainties $u(\vec{r})$. For example, due to (a) above, $u(\vec{r})$ will be small (e.g. 0.01 g/cm$^3$) for $\vec{r}$ values (that is, locations) near the surface and near the boreholes, but far larger (e.g. 0.2 g/cm$^3$) for $\vec{r}$ values in regions that were not directly sampled.

We will also assume that the muon data from each detector is binned in the 2D space of incoming angles, which is then translated into the indicated directional weight for the k-th detector in bin i,j: $m_{ijk}$.

The space of considered density maps is that of a uniform density per voxel, with uniform cubic voxels with sides of length L, so that the density map T is a set of numbers $t_{abc}$ with the indices a,b, and c defining the 3D location of the voxel.

The expected mass density can them be approximated as $x_{ijk} = \Sigma t_{abc} l_{abcijk}$, where the sum is over the voxels in the path indicated by ijk, and $0 < l_{abcijk} \leq L(\sin\theta)^{-1}$ is the average length, through the voxel abc, of the paths that end up in bin i,j of the k-th detector. The averaging is over the possible directions of the muons incoming to the bin. The averaging takes into account the angular resolution, where the dominant term is simply the size of the bin, but also includes additional deviations due to scattering in the rock near the detector and due to the detectors limited angular resolution.

Figure 13:
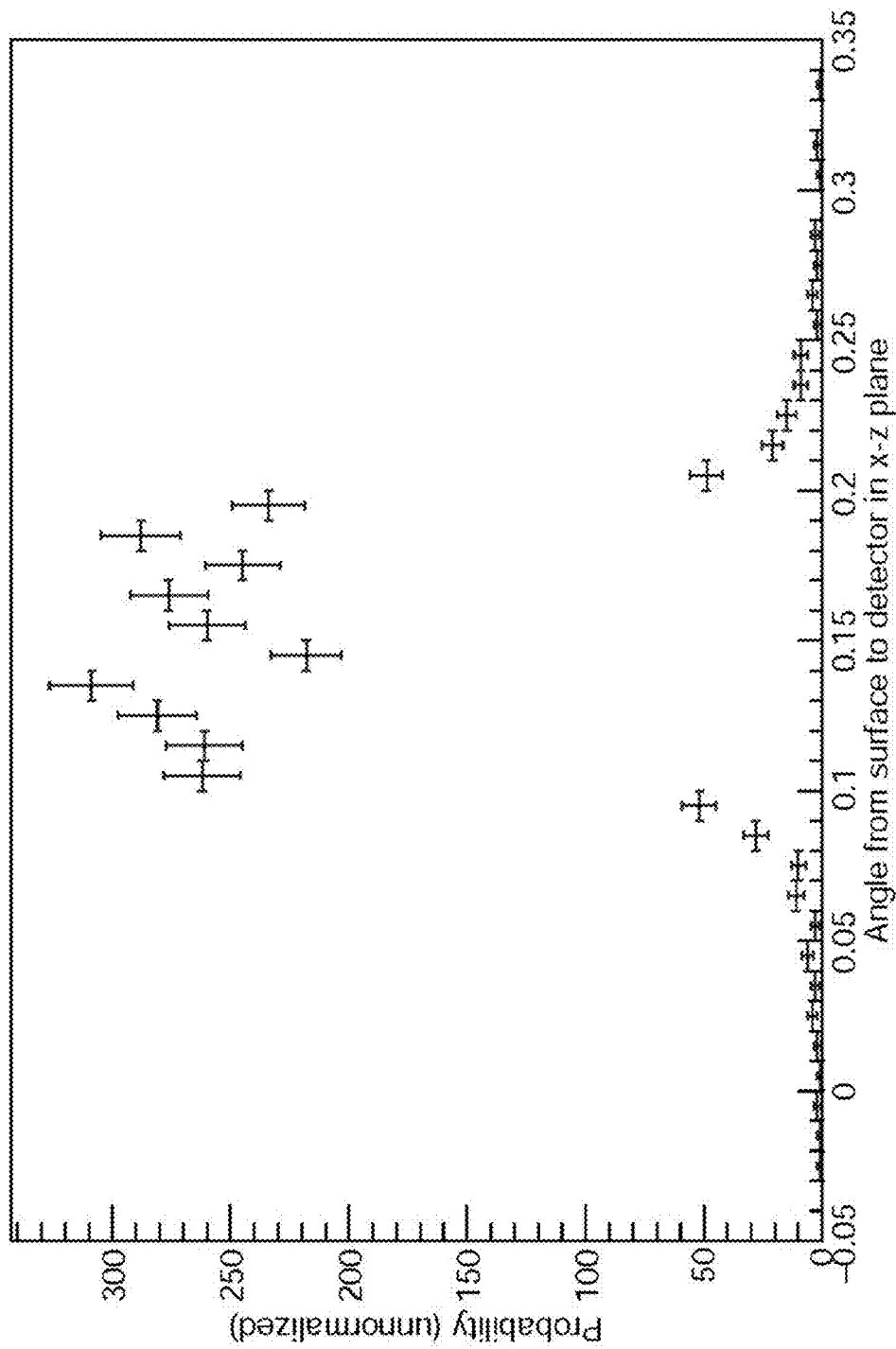
FIG. 13 illustrates angular resolution according to an embodiment of the invention.

The angular resolution is demonstrated in FIG. 13 using a Monte-Carlo simulation of cosmic-ray muons that reach a detector located beneath 10 m of rock. Only muons measured as belonging in the angular bin with $0.1 < \sin\theta\cos\varphi < 0.2$ and $0.1 < \sin\theta\sin\varphi < 0.2$ are included in this sample, where $\theta$ is the zenith angle and $\varphi$ is the azimuthal angle. The figure shows the simulated probability distribution for the angle in the x-z plane of the path from the ground surface to the detector. As described above, most muons arrive from the paths that nominally below to the bin, from 0.1 to 0.2. The small additional deviations due to scattering in the rock and the detector resolution are also visible, in the tails of the distribution outside this range.

We can then present the mapping as a maximization problem seeking to maximize the likelihood $L(C;T) = D(C; T) + R(T)$, where C is the muon data, $D(C;T)$ is the data-likelihood term and R (T) is the regularization term. The data-likelihood term factorizes to $D(C; T) = \Pi L(m_{ijk};T)$, where the multiplication is over all muon data (that is, the ijk indices) and $L(m_{ijk};T) = G(m_{ijk} - x_{ijk}, x_{ijk}^{1/2})$ where $G(x, \sigma)$ is the value of a Gaussian distribution function centered at 0 at location x. The regularization term T can have a form such as $T = \lambda \Pi T_{abc}$, where $\lambda \geq 0$ is the regularization strength, $T_{abc} = G(t_{abc} - m_{abc}; u_{abc})$, where $m_{abc}$ and $u_{abc}$ are the averages of $m(\vec{r})$ and $u(\vec{r})$ over the voxel abc. The regularization strength can be optimized through the standard techniques, such as the L-curve technique. This ensures that in the voxels where the ground density was well-known from previous measurements, and thus $u(\vec{r})$ and $u_{abc}$ are small, the resulting map T will be constrained to be close to the a-priori well-known density $m(\vec{r})$, while in voxels where the density was not well-known from other measurements, the muon data will dominate.

Any gravitometry data B is included using the same formalism, since it too measures the density in a linear combination of voxels. Given the i-th gravitometry measurement taken in location 4, expressed as an observed mass density $M_i$ (analogous to the $m_{ijk}$ above), we calculate the expected mass density as $y_i = \Sigma t_{abc} g_{abci}$, where the sum is over all voxels, and $g_{abci}$ (analogous to $l_{abcijk}$ above) is the average of the distance between a point in the voxel abc and the location of the i-th gravitometry measurement:

$$g_{abci} = \int \frac{1}{\|\vec{r} - \vec{r}_i\|^2} d\vec{r},$$

where the integration is over the voxel abc.

However, while for muon data the dominant error is statistical (hence the $x_{ijk}^{1/2}$ term above) due to the limited muon flux, for gravitometry data the dominant uncertainty is systematic, due to variations in the density within the voxels nearest to the gravitometer. Therefore we include the gravitometry data $B = \{M_i\}$ by adding the data-likelihood term $D_g(B; T) = \Pi L(M_i; T)$, where $L(M_i; T) = G(M_i - y_i, u_i)$, where $u_i$ is the uncertainty on the expected mass density near the i-th gravitometry measurement. The estimation of $u_i$ can be based on generic geophysical parameters, or on data specific for the site. For example, given plenty of gravitometry measurements it is possible to first perform a gravitometry-only mapping for the top-most layers using a finer grid than the grid used for the muon mapping. The variations between the values of voxels in the finer grid that belong the same voxel in the muon-mapping grid indicate the systematic uncertainty for the gravitometry measurements nearest this voxel.

Further regularization terms that favor gradual changes in the density can be added (see [Bryman et al., 2014]), as motivated by the geophysical knowledge of the site. For example, rapid horizontal changes below the soil layer may be disfavored. Or any deviation from the known host rock density can be disfavored below some depth chosen to avoid the soil. These a-priori expectations of gradual changes in the density arise from a geophysical model of the ground. The formulations in the prior art arise from an unrealistically simple model that neglects the spatial dependence of these expectation.

The distance scales on which we (a-priori) expect the density to change vary by location. This may be due to:
  a. Differences between soil structure in the upper layer and rock structure below. For example, in a building site the soil layers may have already been disturbed artificially and may admit rapid changes, so that small scales should be used for low depths.
  b. The presence of geologically recent sedimentary layers in certain sub volumes indicates large scales for horizontal changes and small scales for vertical changes.
  c. Prior information on the presence or absence of intrusions. For example, intrusions can have precursors which can be identified in bore samples. When a particular bore hole sample indicates a precursor, rapid changes in all directions should be allowed.

For example, expecting vertical variations of scale $v(\vec{r})$ and horizontal variations of scale $h(\vec{r})$, with both depending on the location $\vec{r}$, and using the same symbols as before, we add a regularization term for the abc-th voxel, so $T = \lambda \Pi T_{abc} D_{abc}$, where $D_{abc} = G(t_{abc} - t_{a+1,b,c}; h_{abc}) G(t_{abc} - t_{a,b+1,c}; h_{abc}) G(t_{abc} - t_{a,b,c+1}; v_{abc})$ and $h_{abc}$ and $v_{abc}$ are the averages of $h(\vec{r})$ and $v(\vec{r})$ in the abc-th voxel.

In other frameworks, the $u(\vec{r})$ must be introduced differently. For example, in the resolving kernel approach, using the nomenclature of [Jourde, Gibert, Marteau 2014], both the weighting functions w(r', r") used to define the acquisition kernels and the weights $W_k$ given to the individual measurements should be modified. The $W_k$ weights, which in the prior art are the inverse of the various experimental errors, should be modified to be the inverse of the total errors, including the appropriate kernel-weighted integral of $u(\vec{r})$. Again, any gravimetry data can naturally be included with the muon data with trivial modification. This was demonstrated for the resolving kernel approach in [Jourde, Gibert, Marteau 2014].

Figure 14:
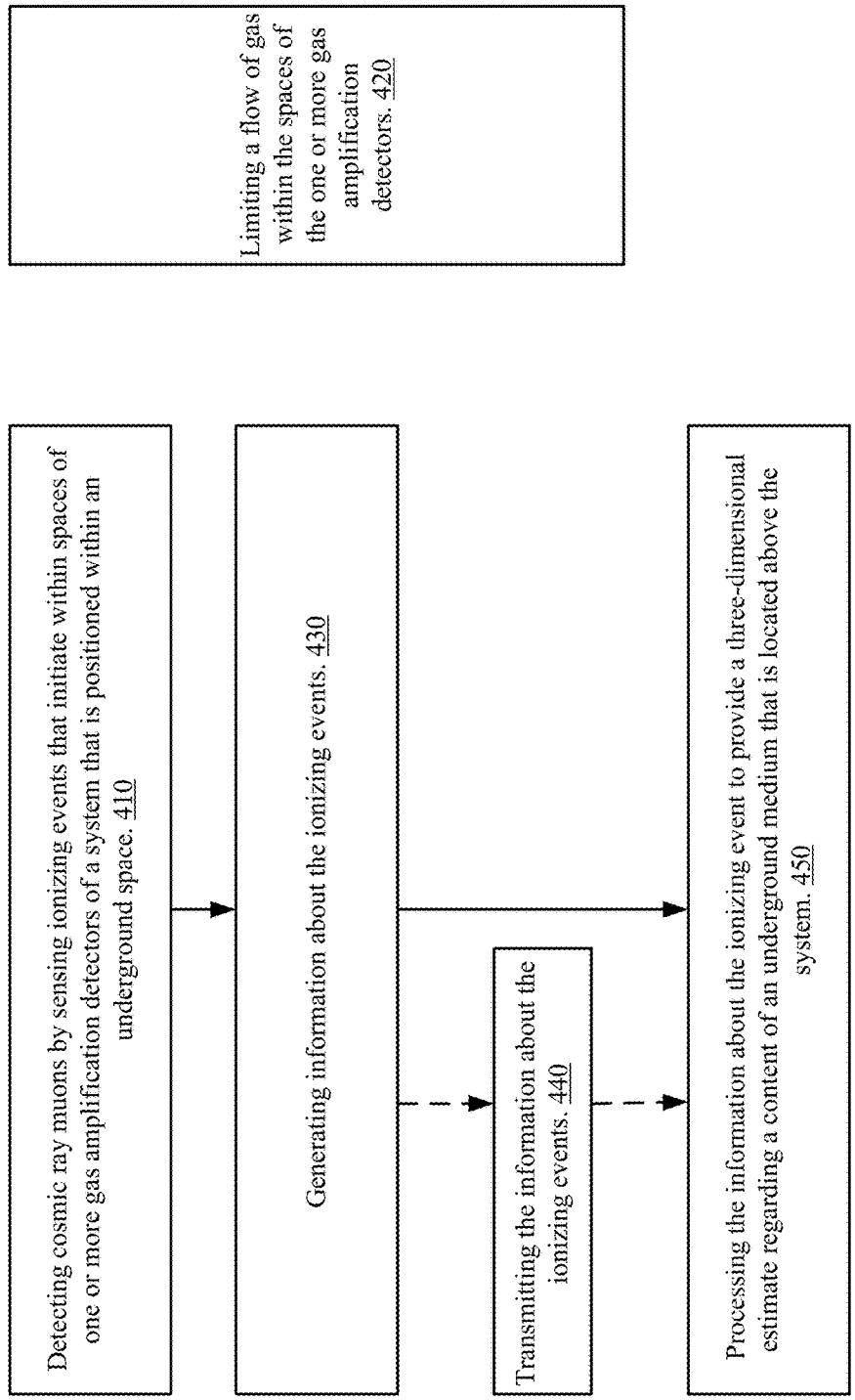
FIG. 14 illustrates a method according to an embodiment of the invention.

FIG. 14 illustrates method 400 according to an embodiment of the invention.

Method 400 is for underground exploration using cosmic rays muons.

Method 400 include step 410 of detecting cosmic ray muons by sensing ionizing events that initiate within spaces of one or more gas amplification detectors of a system that is positioned within an underground space and step 420 of limiting a flow of gas within the spaces of the one or more gas amplification detectors.

Step 420 may be executed in parallel to step 410, in a partially overlapping manner or in an overlapping manner.

Step 420 may include at least one out of:
a. Preventing the flow of the gas by positioning the one or more gas amplification detectors within a sealed housing.
b. Limiting the flow of the gas by positioning the one or more gas amplification detectors within a sealed housing.
c. Limiting a rate of the flow of the gas to below 5 liter a day.
d. Limiting the gas flow to each gas vessel to a rate that suffices to replace the gas within it every few days or hours.
e. Cleaning, by forcing a flow of the gas through the one or more spaces of the one or more gas amplification detectors, during multiple cleaning periods, wherein each cleaning period is followed by a non-flow period during which the flow of cleaning gas is stopped. The duration of a non-flow period exceeds (for example of a factor of at least ten) a duration of the cleaning period.
f. Providing a gas amplification detector of the one or more gas amplification detectors comprises outgassing materials that limit a total outgassing rates of the gas amplification detector below $5 \cdot 10^{-5}$ cc atmosphere per second.
g. Providing a gas amplification detector of the one or more gas amplification detectors comprises at least one seal that exhibits a lower permeability than a Nitrile Rubber seal.
h. Providing a gas amplification detector of the one or more gas amplification detectors comprises one or more internal component that is made of Polyether ether ketone.
i. Passing the gas through a first manifold positioned at one end of a gas amplification detector of the one or more gas amplification detectors, over multiple front-end electronics and through a drift gap and to a second manifold that is positioned at an opposite edge of the gas amplification detector.
j. Passing the gas through a manifold of the first and second manifold that has an opening that has a height that changes as a function of a distance from a center of the manifold.
k. Preventing the flow of the gas within the spaces of the one or more gas amplification detectors.
l. Supplying the gas from an underground pressurized gas vessel.
m. Evacuating the gas using a pump.
n. Maintaining, by a pump, a gas pressure of 0.2-0.9 atmospheres in the detector.

Step 420 may be followed by at least one of the following steps:
a. Generating information about the ionizing events (430).
b. Transmitting the information about the ionizing events (440). The information is transmitted outside the system—for example to an above the ground system.
c. Processing the information about the ionizing event to provide a three-dimensional estimate regarding a content of an underground medium that is located above the system (450). The processing may be executed regardless of step 440.

Step 450 may include at least one of the following:
a. Processing that is responsive to information that was gained by another system, about the content of the underground medium. The other system may include one or more sensors that differ from gas amplification detectors.
b. Performing data fusion of the information about the ionizing events and Ground-Penetrating Radar data related to a content of at least an upper portion of the underground medium. The data fusion may be responsive to a reference three-dimensional model of the underground medium.
c. Processing that is responsive to at least one property of a cavity (for example borehole) containing the system. For example—if there is a gap between the system and the sidewalls of the cavity or not—as the gap attenuates the signals.
d. Performing data fusion that is responsive to uncertainties of a reference model and to dependence of said uncertainties on location.
e. Performing mapping using an explicit regularization term that quantifies a disagreement between the map and the a-priori model.
f. Generating inverted data related to the underground model.
g. Performing data fusion between the inverted data and information that was gained by another system, about the content of the underground medium.
h. Performing data fusion that includes using information about uncertainties related to the inverted data. For example—the GPR map is valid between the surface and a certain depth. Voxels below that certain depth may be associated with a low reliability factor.
i. Applying a mapping algorithm that uses resolving kernels with weighting functions that reflect uncertainties related to the inverted data.

Step 450 may include any of the steps illustrated in the above text—especially the section of this specification titled "mapping".

Figure 15:
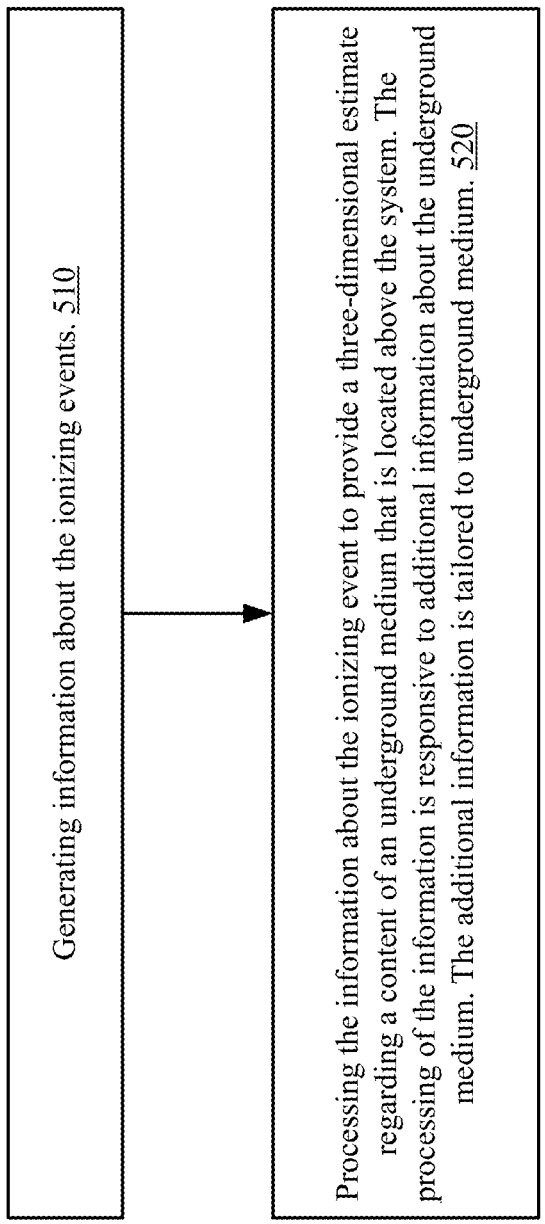
FIG. 15 illustrates a method according to an embodiment of the invention.

FIG. 15 illustrates method 500 according to an embodiment of the invention.

Method 500 is for underground exploration using cosmic rays muons, the method comprises: detecting cosmic ray muons by sensing ionizing events that initiate within spaces of one or more gas amplification detectors of a system that is positioned within an underground space.

Method 500 may start by step 510 of generating information about the ionizing events.

Step 510 may be followed by step 520 of processing the information about the ionizing event to provide a three-dimensional estimate regarding a content of an underground medium that is located above the system. The processing of the information is responsive to additional information about the underground medium.

The additional information is tailored to underground medium and may be obtained from an information source that differs from the ionizing events.

The information source may be another system (such as a GPR, a chemical analysis of a sample taken from the underground medium or from the content that was excavated to form the borehole in which the system is inserted) from geological information and the like.

The additional information is tailored to the underground medium (that is being estimated) in the sense that the additional information differs from a general information or a general model that is used for each monitored underground volume-regardless of the specific properties of the underground volume that is being estimated.

The additional information may be any type of information mentioned in step 450.

Step 520 may include any of the steps illustrated in the above text-especially the section of this specification titled "mapping".

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements.

The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A method, for evaluating an underground medium, the method comprises:
   positioning a system within an underground space and below the underground medium;
   detecting cosmic ray muons by sensing ionizing events that occur within one or more spaces of one or more gas amplification detectors of the system;
   generating, by the system, information about the ionizing events; and
   processing the information about the ionizing event to provide a three-dimensional estimate regarding the content of the underground medium, wherein the processing comprises performing a data fusion of the information about the ionizing events and Ground-Penetrating Radar data related to a content of at least an upper portion of the underground medium.

2. The method according to claim 1 comprising limiting a flow of gas within the one or more spaces of the one or more gas amplification detectors.

3. The method according to claim 2 wherein the method comprises limiting a rate of the flow of the gas to below 5 liters a day.

4. The method according to claim 2, wherein the method comprises cleaning, by forcing a flow of the gas through the one or more spaces of the one or more gas amplification detectors, during multiple cleaning periods, wherein each cleaning period is followed by a non-flow period during which the flow of cleaning gas is stopped; and wherein a duration of a non-flow period exceeds a duration of the cleaning period.

5. The method according to claim 2 comprising passing the gas through a first manifold configured to accept the gas from a gas inlet and to split the gas flow to several gas outlets that are positioned at one end of a main gas volume of each of the one or more gas amplification detectors, through and throughout the main gas volumes of each of the one or more gas amplification detectors and to a second manifold that is configured to collect the gas through several gas inlets that are positioned at an opposite edge of the main gas volumes and to pass the gas flow to a gas outlet.

6. The method according to claim 2 wherein the limiting of the flow of gas comprises preventing the flow of the gas by positioning the one or more gas amplification detectors within a sealed housing.

7. The method of claim 2 comprising supplying the gas from an underground pressurized gas vessel.

8. The method of claim 2 comprising evaluating the gas using a pump.

9. The method of claim 8 wherein the pump maintains a gas pressure of 0.2-0.9 atmospheres in the detector.

10. The method according to claim 1 wherein the one or more gas amplification detectors comprise at least one thick gaseous electron multiplier (ThGEM) detector.

11. The method according to claim 1 wherein the data fusion is responsive to a reference three-dimensional model of the underground medium.

12. The method according to claim 1 wherein the processing is responsive to at least one property of a cavity containing the system.

13. The method according to claim 1 wherein the data fusion is responsive to uncertainties of a reference model and to dependence of said uncertainties on location.

14. The method according to claim 1 further comprising generating inverted data related to the underground model.

15. The method according to claim 14 wherein the data fusion comprises using information about uncertainties related to geo-physical information.

16. A system that comprises: a first manifold; one or more gas amplification detectors that comprise one or more spaces; wherein the one or more gas amplification detectors are configured to detect cosmic ray muons by sensing ionizing events that occur within the one or more spaces; wherein the first manifold is positioned on one end of a gas amplification detector of the one or more gas amplification detectors; wherein the first manifold comprises a gas entrance located at a center of the first manifold, an exit slot and an inner gas path that is configured to fluidly couple the gas entrance to the exit slot; wherein the exit slot spans across a majority of one face of the first manifold; wherein a height of the inner gas path leading to the exit slot at the center of the first manifold is smaller than a height of the exit slot outside the center of the first manifold; and wherein the exit slot is configured to face the one or more spaces where the gas amplification detectors sense the ionizing events.

17. A computer program product that stores instructions that once executed by a computer cause the computer to execute the steps of: detecting cosmic ray muons that passed through an underground medium by sensing ionizing events that occur within one or more spaces of one or more gas amplification detectors; generating information about the ionizing events; processing the information about the ionizing event to provide a three-dimensional estimate regarding the content of the underground medium, wherein the processing comprises performing a data fusion of the information about the ionizing events and Ground-Penetrating Radar data related to a content of at least an upper portion of the underground medium.

* * * * *